United States Patent
Amemiya et al.

(10) Patent No.: US 8,722,046 B2
(45) Date of Patent: May 13, 2014

(54) HUMAN MONOCLONAL ANTIBODIES PROTECTIVE AGAINST BUBONIC PLAGUE

(75) Inventors: Kei Amemiya, Rockville, MD (US); Dimiter S. Dimitrov, Frederick, MD (US); Xiaodong Xiao, Frederick, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/260,413

(22) PCT Filed: Apr. 8, 2010

(86) PCT No.: PCT/US2010/001051
§ 371 (c)(1),
(2), (4) Date: Dec. 14, 2011

(87) PCT Pub. No.: WO2010/117455
PCT Pub. Date: Oct. 14, 2010

(65) Prior Publication Data
US 2012/0114656 A1 May 10, 2012

Related U.S. Application Data

(60) Provisional application No. 61/212,166, filed on Apr. 8, 2009.

(51) Int. Cl.
*A61K 39/395* (2006.01)
*C12P 21/08* (2006.01)
*A61K 39/40* (2006.01)

(52) U.S. Cl.
USPC ............... 424/142.1; 424/150.1; 530/388.15; 530/388.2

(58) Field of Classification Search
None
See application file for complete search history.

(56) References Cited

U.S. PATENT DOCUMENTS

2006/0093609 A1* 5/2006 Hill et al. ................... 424/164.1

OTHER PUBLICATIONS

MacCallum et al ,J. Mol. Biol., 262,732-745, 1996.*
Casset et al ,Biochemical and Biophysical Research Communications, 307:198-205, 2003.*
Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M. ,Research in Immunology, 145:33-36, 1994.*
Bendig M. M. Methods: A Companion to Methods in Enzymology, 1995; 8:83-93.*

* cited by examiner

*Primary Examiner* — Padma V Baskar
(74) *Attorney, Agent, or Firm* — Elizabeth Arwine

(57) ABSTRACT

In this application are described fully human monoclonal antibodies which specifically recognize F1 or V antigen of *Y. pestis* and epitopes recognized by these monoclonal antibodies. Also provided are mixtures of antibodies of the present invention, as well as methods of using individual antibodies or mixtures thereof for the detection, prevention, and/or therapeutical treatment of plague infections in vitro and in vivo.

16 Claims, 8 Drawing Sheets

1a

1b

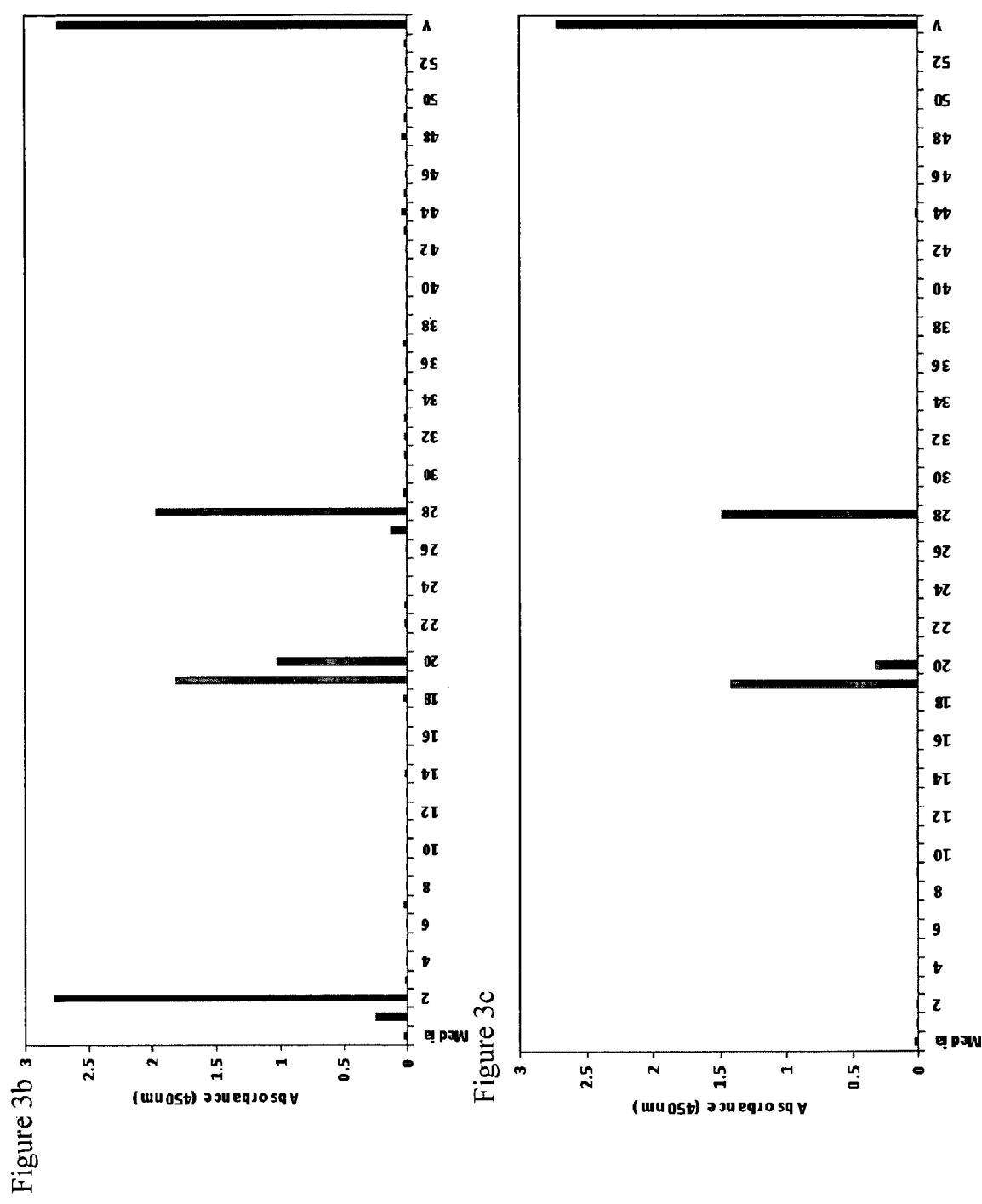

SEQUENCE LISTING

<160> NUMBER OF SEQ ID NOS: 16

<210> SEQ ID NO 1
<211> LENGTH: 17
<212> TYPE: PRT
<213> ORGANISM: Artificial sequence
<220> FEATURE:
<223> OTHER INFORMATION: Y. pestis F1 antigen peptide

<400> SEQUENCE: 1

Met Lys Lys Ile Ser Ser Val Ile Ala Ile
                 5                   10

Ala Leu Phe Gly Thr Ile Ala
                 15

<210> SEQ ID NO 2
<211> LENGTH: 17
<212> TYPE: PRT
<213> ORGANISM: Artificial sequence
<220> FEATURE:
<223> OTHER INFORMATION: Y. pestis F1 antigen peptide

<400> SEQUENCE: 2

Val Ile Ala Ile Ala Leu Phe Gly Thr Ile
                 5                   10

Ala Thr Ala Asn Ala Ala Asp
                 15

<210> SEQ ID NO 3
<211> LENGTH: 231
<212> TYPE: PRT
<213> ORGANISM: Artificial sequence
<220> FEATURE:
<223> OTHER INFORMATION: Heavy chain m252 antibody

<400> SEQUENCE: 3

Glu Val Gln Leu Val Gln Ser Gly Ala Glu
                 5                   10

Val Lys Lys Pro Gly Ala Ser Val Lys Val
                 15                  20

Ser Cys Lys Ala Ser Gly Tyr Thr Phe Thr
                 25                  30

Gly Tyr Tyr Met His Trp Val Arg Gln Ala
            35                  40

Pro Gly Gln Gly Leu Glu Trp Met Gly Arg
            45                  50

Ile Asn Pro Asn Ser Gly Gly Thr Asn Tyr
            55                  60

Ala Gln Lys Phe Gln Gly Arg Val Thr Met
            65                  70

Thr Arg Asp Thr Ser Ile Ser Thr Ala Tyr
            75                  80

Met Glu Leu Ser Arg Leu Arg Ser Asp Asp
            85                  90

Thr Ala Val Tyr Tyr Cys Ala Arg Glu Arg
            95                  100

Tyr Gln Leu Leu Ser Asp Tyr Tyr Tyr Gly
            105                 110

Met Asp Val Trp Gly Gln Gly Thr Thr Val
            115                 120

Thr Val Ser Ser Ala Ser Thr Lys Gly Pro
            125                 130

Ser Val Phe Pro Leu Ala Pro Ser Ser Lys
            135                 140

Ser Thr Ser Gly Gly Thr Ala Ala Leu Gly
            145                 150

Cys Leu Val Lys Asp Tyr Phe Pro Glu Pro
            155                 160

Val Thr Val Ser Trp Asn Ser Gly Ala Leu
            165                 170

Thr Ser Gly Val His Thr Phe Pro Ala Val
            175                 180

Leu Gln Ser Ser Gly Leu Tyr Ser Leu Ser
            185                 190

Ser Val Val Thr Val Pro Ser Ser Ser Leu
            195                 200

Gly Thr Gln Thr Tyr Ile Cys Asn Val Asn
            205                 210

His Lys Pro Ser Asn Thr Lys Val Asp Lys
            215                 220

Lys Val Glu Pro Lys Ser Cys Asp Lys Thr
            225                 230

Ser

<210> SEQ ID NO 4
<211> LENGTH: 693
<212> TYPE: DNA
<213> ORGANISM: Artificial sequence
<220> FEATURE:
<223> OTHER INFORMATION: Heavy chain m252 antibody

<400> SEQUENCE: 4
gaggtgcagc tggtacagtc tggggctgag gtgaagaagc           40
ctggggcctc agtgaaggtc tcctgcaagg cttctggata           80
caccttcacc ggctactata tgcactgggt gcgacaggcc           120
cctggacaag ggcttgagtg gatgggacgg atcaaccta            160

-continued

| | |
|---|---|
| acagtggtgg cacaaactat gcacagaagt ttcagggcag | 200 |
| ggtcaccatg accagggaca cgtccatcag cacagcctac | 240 |
| atggagctga gcaggctgag atctgacgac acggccgtgt | 280 |
| attactgtgc gagagaaagg taccagctgc tatcagacta | 320 |
| ctactacggt atggacgtct ggggccaagg gaccacggtc | 360 |
| accgtctcct cagcctccac caagggccca tcggtcttcc | 400 |
| ccctggcacc ctcctccaag agcacctctg ggggcacagc | 440 |
| ggccctgggc tgcctggtca aggactactt ccccgaaccg | 480 |
| gtgacggtgt cgtggaactc aggcgccctg accagcggcg | 520 |
| tgcacacctt cccggctgtc ctacagtcct caggactcta | 560 |
| ctccctcagc agcgtggtga ccgtgccctc agcagcttg | 600 |
| ggcacccaga cctacatctg caacgtgaat cacaagccca | 640 |
| gcaacaccaa ggtggacaag aaagttgagc ccaaatcttg | 680 |
| tgacaaaact agt | 693 |

```
<210> SEQ ID NO 5
<211> LENGTH: 214
<212> TYPE: PRT
<213> ORGANISM: Artificial sequence
<220> FEATURE:
<223> OTHER INFORMATION: Light chain m252 antibody

<400> SEQUENCE: 5
```

Asp Ile Gln Met Thr Gln Ser Pro Ser Thr
                5                   10

Leu Ser Ala Ser Val Gly Asp Arg Val Thr
                15                  20

Ile Thr Cys Arg Ala Ser Gln Gly Ile Gly
                25                  30

Asn Tyr Leu Ala Trp Ile Gln Gln Lys Pro
                35                  40

Gly Thr Ala Pro Lys Ser Leu Val Tyr Ala
                45                  50

Ala Ser Arg Leu Glu Ser Gly Val Pro Ser
                55                  60

Arg Phe Ser Gly Ser Gly Ser Gly Thr Asp
                65                  70

Phe Thr Leu Thr Ile Thr Ser Leu Gln Pro
                75                  80

Glu Asp Phe Ala Thr Tyr Phe Cys Gln Gln
                85                  90

Tyr Leu Ser Tyr Pro Ile Thr Phe Gly Gln
                95                  100

Gly Thr Arg Leu Glu Ile Lys Arg Thr Val
                105                 110

Ala Ala Pro Ser Val Phe Ile Phe Pro Pro
                115                 120

Ser Asp Glu Gln Leu Lys Ser Gly Thr Ala
                125                 130

Ser Val Val Cys Leu Leu Asn Asn Phe Tyr
                135                 140

Pro Arg Glu Ala Lys Val Gln Trp Lys Val
                145                 150

Asp Asn Ala Leu Gln Ser Gly Asn Ser Gln
                155                 160

Glu Ser Val Thr Glu Gln Asp Ser Lys Asp
                165                 170

Ser Thr Tyr Ser Leu Ser Ser Thr Leu Thr
                175                 180

Leu Ser Lys Ala Asp Tyr Glu Lys His Lys
                185                 190

Leu Tyr Ala Cys Glu Val Thr His Gln Gly
                195                 200

Leu Ser Ser Pro Val Thr Lys Ser Phe Asn
                205                 210

Arg Gly Glu Cys

<210> SEQ ID NO 6
<211> LENGTH: 645
<212> TYPE: DNA
<213> ORGANISM: Artificial sequence
<220> FEATURE:
<223> OTHER INFORMATION: Light chain m252 antibody

<400> SEQUENCE: 6

```
gacatccaga tgacccagtc tccatccacc ctgtctgcat       40
ctgtaggaga cagagtcacc atcacttgtc gggcgagtca       80
gggcattggg aattatttag cctggattca gcagaaacca      120
gggacagccc ctaagtccct ggtctacgcc gcatctcgtt      160
tggaaagtgg ggtcccatca agattcagcg gcagtggatc      200
tgggacagat ttcactctca ccatcaccag cctgcagcct      240
gaagattttg caacctattt ctgccaacaa tatcttagtt      280
acccgatcac cttcggccaa gggacacgac tggagattaa      320
acgaactgtg gctgcaccat ctgtcttcat ctttccgcca      360
tctgatgagc agttgaaatc tggaactgcc tctgttgtgt      400
gcctgctgaa taacttctat cccagagagg ccaaagtaca      440
gtggaaggtg gataacgccc tccaatcggg taactcccag      480
gagagtgtca cagagcagga cagcaaggac agcacctaca      520
gcctcagcag caccctgacg ctgagcaaag cagactacga      560
gaaacacaaa gtctacgcct gcgaagtcac ccatcagggc      600
ctgagctcgc ccgtcacaaa gagcttcaac aggggagagt      640
gttaa                                            645
```

<210> SEQ ID NO 7
<211> LENGTH: 17
<212> TYPE: PRT
<213> ORGANISM: Artificial sequence
<220> FEATURE:
<223> OTHER INFORMATION: Y. pestis V antigen peptide

<400> SEQUENCE: 7

Met Ile Arg Ala Tyr Glu Gln Asn Pro Gln
                5                  10

-continued

```
His Phe Ile Glu Asp Leu Glu
                15

<210> SEQ ID NO 8
<211> LENGTH: 17
<212> TYPE: PRT
<213> ORGANISM: Artificial sequence
<220> FEATURE:
<223> OTHER INFORMATION: Y. pestis V antigen peptide

<400> SEQUENCE: 8

Glu Gln Asn Pro Gln His Phe Ile Glu Asp
                5                   10

Leu Glu Lys Val Arg Val Glu
                15

<210> SEQ ID NO 9
<211> LENGTH: 223
<212> TYPE: PRT
<213> ORGANISM: Artificial sequence
<220> FEATURE:
<223> OTHER INFORMATION: Heavy chain m253 antibody

<400> SEQUENCE: 9

Glu Val Gln Leu Val Gln Ser Gly Ala Glu
                5                   10

Val Lys Lys Pro Gly Ala Ser Val Lys Val
                15                  20

Ser Cys Lys Ala Ser Gly Tyr Thr Phe Thr
                25                  30

Ser Tyr Gly Ile Ser Trp Val Arg Gln Ala
                35                  40

Pro Gly Gln Gly Leu Glu Trp Met Gly Trp
                45                  50

Ile Ser Ala Tyr Asn Gly Asn Thr Asn Tyr
                55                  60

Ala Gln Lys Leu Gln Gly Arg Val Thr Met
                65                  70

Thr Thr Asp Thr Ser Thr Ser Thr Ala Tyr
                75                  80

Met Glu Leu Arg Ser Leu Arg Ser Asp Asp
                85                  90

Thr Ala Val Tyr Tyr Cys Ala Arg Val Ala
                95                  100

Arg Ala Phe Asp Ile Trp Gly Gln Gly Thr
                105                 110

Thr Val Thr Val Ser Ser Ala Ser Thr Lys
                115                 120

Gly Pro Ser Val Phe Pro Leu Ala Pro Ser
                125                 130

Ser Lys Ser Thr Ser Gly Gly Thr Ala Ala
                135                 140

Leu Gly Cys Leu Val Lys Asp Tyr Phe Pro
                145                 150

Glu Pro Val Thr Val Ser Trp Asn Ser Gly
                155                 160

Ala Leu Thr Ser Gly Val His Thr Phe Pro
                165                 170
```

```
Ala Val Leu Gln Ser Ser Gly Leu Tyr Ser
            175                 180

Leu Ser Ser Val Val Thr Val Pro Ser Ser
            185                 190

Ser Leu Gly Thr Gln Thr Tyr Ile Cys Asn
            195                 200

Val Asn His Lys Pro Ser Asn Thr Lys Val
            205                 210

Asp Lys Lys Val Glu Pro Lys Ser Cys Asp
            215                 220

Lys Thr Ser

<210> SEQ ID NO 10
<211> LENGTH: 669
<212> TYPE: DNA
<213> ORGANISM: Artificial sequence
<220> FEATURE:
<223> OTHER INFORMATION: Heavy chain m253 antibody

<400> SEQUENCE: 10
gaagtgcagc tggtgcagtc tggagctgag gtgaagaagc        40
ctggggcctc agtgaaggtc tcctgcaagg cctctggtta        80 caccttttacc agctatggta tcagctgggt gcgacaggcc      120
cctggacaag ggcttgagtg gatgggatgg atcagcgctt       160
acaatggtaa cacaaactat gcacagaagc tccagggcag       200
agtcaccatg accacagaca catccacgag cacagcctac       240
atggagctga ggagcctgag atctgacgac acggccgtgt       280
attactgtgc gagggtggct cgggcttttg atatctgggg       320
ccaagggacc acggtcaccg tctcctcagc ctccaccaag       360
ggcccatcgg tcttccccct ggcaccctcc tccaagagca       400
cctctggggg cacagcggcc ctgggctgcc tggtcaagga       440
ctacttcccc gaaccggtga cggtgtcgtg gaactcaggc       480
gccctgacca gcggcgtgca caccttcccg gctgtcctac       520
agtcctcagg actctactcc ctcagcagcg tggtgaccgt       560
gccctccagc agcttgggca cccagaccta catctgcaac       600
gtgaatcaca agcccagcaa caccaaggtg gacaagaaag       640
ttgagcccaa atcttgtgac aaaactagt                    669

<210> SEQ ID NO 11
<211> LENGTH: 214
<212> TYPE: PRT
<213> ORGANISM: Artificial sequence
<220> FEATURE:
<223> OTHER INFORMATION: Light chain m253 antibody

<400> SEQUENCE: 11

Asp Thr Gln Met Thr Gln Ser Pro Ser Phe
            5                    10

Leu Ser Ala Ser Val Gly Asp Arg Val Thr
            15                   20

Ile Thr Cys Arg Ala Ser Gln Gly Ile Ser
            25                   30
```

Ser Tyr Leu Ala Trp Tyr Gln Gln Lys Pro
                35                  40

Gly Lys Ala Pro Lys Leu Leu Ile Tyr Ala
                45                  50

Ala Ser Thr Leu Gln Ser Gly Val Pro Ser
                55                  60

Arg Phe Ser Gly Ser Gly Ser Gly Thr Glu
                65                  70

Phe Thr Leu Thr Ile Ser Ser Leu Gln Pro
                75                  80

Glu Asp Phe Ala Thr Tyr Tyr Cys Gln Gln
                85                  90

Leu Asn Ser Tyr Pro Leu Thr Phe Gly Pro
                95                 100

Gly Thr Lys Val Asp Ile Lys Arg Thr Val
               105                 110

Ala Ala Pro Ser Val Phe Ile Phe Pro Pro
               115                 120

Ser Asp Glu Gln Leu Lys Ser Gly Thr Ala
               125                 130

Ser Val Val Cys Leu Leu Asn Asn Phe Tyr
               135                 140

Pro Arg Glu Ala Lys Val Gln Trp Lys Val
               145                 150

Asp Asn Ala Leu Gln Ser Gly Asn Ser Gln
               155                 160

Glu Ser Val Thr Glu Gln Asp Ser Lys Asp
               165                 170

Ser Thr Tyr Ser Leu Ser Ser Thr Leu Thr
               175                 180

Leu Ser Lys Ala Asp Tyr Gly Lys His Lys
               185                 190

Leu Tyr Ala Cys Glu Val Thr His Gln Gly
               195                 200

Leu Ser Ser Pro Val Thr Lys Ser Phe Asn
               205                 210

Arg Gly Glu Cys

<210> SEQ ID NO 12
<211> LENGTH: 645
<212> TYPE: DNA
<213> ORGANISM: Artificial sequence
<220> FEATURE:
<223> OTHER INFORMATION: Light chain m253 antibody

<400> SEQUENCE: 12
gacacccaga tgacccagtc tccatccttc ctgtctgcat         40
ctgtaggaga cagagtcacc atcacttgcc gggccagtca         80
gggcattagc agttatttag cctggtatca gcaaaaacca        120
gggaaagccc ctaagctcct gatctatgct gcatccactt        160
tgcaaagtgg ggtcccatca aggttcagcg gcagtggatc        200
tgggacagaa ttcactctca caatcagcag cctgcagcct        240
gaagattttg caacttatta ctgtcaacag cttaatagtt        280

-continued

```
accctctcac tttcggccct gggaccaaag tggatatcaa        320
acgaactgtg gctgcaccat ctgtcttcat cttcccgcca        360
tctgatgagc agttgaaatc tggaactgcc tctgttgtgt        400
gcctgctgaa taacttctat cccagagagg ccaaagtaca        440
gtggaaggtg gataacgccc tccaatcggg taactcccag        480
gagagtgtca cagagcagga cagcaaggac agcacctaca        520
gcctcagcag caccctgacg ctgagcaaag cagactacga        560
gaaacacaaa ctctacgcct gcgaagtcac ccatcagggc        600
ctgagctcgc ccgtcacaaa gagcttcaac aggggagagt        640
gttaa                                             645
```

<210> SEQ ID NO 13
<211> LENGTH: 226
<212> TYPE: PRT
<213> ORGANISM: Artificial sequence
<220> FEATURE:
<223> OTHER INFORMATION: Heavy chain m254 antibody

<400> SEQUENCE: 13

Glu Val Gln Leu Val Glu Ser Gly Gly Val
                5                   10

Val Val Gln Pro Gly Gly Ser Leu Arg Leu
                15                  20

Ser Cys Ala Ala Ser Gly Phe Thr Phe Asp
                25                  30

Asp Tyr Thr Met His Trp Val Arg Gln Ala
                35                  40

Pro Gly Lys Gly Leu Glu Trp Val Ser Leu
                45                  50

Ile Ser Trp Asp Gly Gly Ser Thr Tyr Tyr
                55                  60

Ala Asp Ser Val Lys Gly Arg Phe Thr Ile
                65                  70

Ser Arg Asp Asn Ser Lys Asn Ser Leu Tyr
                75                  80

Leu Gln Met Asn Ser Leu Arg Thr Glu Asp
                85                  90

Thr Ala Leu Tyr Tyr Cys Ala Lys Gly Pro
                95                  100

Gly Gly Trp Tyr Tyr Phe Asp Tyr Trp Gly
                105                 110

Gln Gly Thr Leu Val Thr Val Ser Ser Ala
                115                 120

Ser Thr Lys Gly Pro Ser Val Phe Pro Leu
                125                 130

Ala Pro Ser Ser Lys Ser Thr Ser Gly Gly
                135                 140

Thr Ala Ala Leu Gly Cys Leu Val Lys Asp
                145                 150

Tyr Phe Pro Glu Pro Val Thr Val Ser Trp
                155                 160

Asn Ser Gly Ala Leu Thr Ser Gly Val His
                165                 170

```
Thr Phe Pro Ala Val Leu Gln Ser Ser Gly
            175                 180

Leu Tyr Ser Leu Ser Ser Val Val Thr Val
            185                 190

Pro Ser Ser Ser Leu Gly Thr Gln Thr Tyr
            195                 200

Ile Cys Asn Val Asn His Lys Pro Ser Asn
            205                 210

Thr Lys Val Asp Lys Lys Val Glu Pro Lys
            215                 220

Ser Cys Asp Lys Thr Ser
            225

<210> SEQ ID NO 14
<211> LENGTH: 678
<212> TYPE: DNA
<213> ORGANISM: Aritificial sequence
<220> FEATURE:
<223> OTHER INFORMATION: Heavy chain m254 antibody

<400> SEQUENCE: 14
gaggtgcagc tggtggagtc cggggagtc gtggtacagc              40 ctgggggtc cctgagactc tcctgtgcag cctctggatt              80 caccttgat gattatacca tgcactgggt ccgtcaagct             120
ccggggaagg gtctggagtg ggtctctctt attagttggg            160
atggtggtag cacatactat gcagactctg tgaagggccg            200
attcaccatc tccagagaca acagcaaaaa ctccctgtat            240
ctgcaaatga acagtctgag aactgaggac accgccttgt            280
attactgtgc aaaaggaccc ggtggctggt actactttga            320
ctactggggc cagggaaccc tggtcaccgt ctcctcagcc            360
tccaccaagg gcccatcggt cttccccctg gcaccctcct            400
ccaagagcac ctctgggggc acagcggccc tgggctgcct            440
ggtcaaggac tacttccccg aaccggtgac ggtgtcgtgg            480
aactcaggcg ccctgaccag cggcgtgcac accttcccgg            520
ctgtcctaca gtcctcagga ctctactccc tcagcagcgt            560
ggtgaccgtg cccctccagca gcttgggcac ccagacctac            600
atctgcaacg tgaatcacaa gcccagcaac accaaggtgg            640
acaagaaagt tgagcccaaa tcttgtgaca aaactagt              678

<210> SEQ ID NO 15
<211> LENGTH: 214
<212> TYPE: PRT
<213> ORGANISM: Artificial sequence
<220> FEATURE:
<223> OTHER INFORMATION: Light chain m254 antibody

<400> SEQUENCE: 15

Asp Ile Gln Met Thr Gln Ser Pro Ser Ser
                5                   10

Leu Ser Ala Ser Val Gly Asp Arg Val Thr
            15                  20

Ile Thr Cys Arg Ala Ser Gln Gly Ile Ser
```

```
                             25                  30
Asn Tyr Leu Ala Trp Tyr Gln Gln Lys Pro
             35                  40
Gly Lys Val Pro Lys Leu Leu Ile Tyr Ala
             45                  50
Ala Ser Thr Leu Gln Ser Gly Val Pro Ser
             55                  60
Arg Phe Ser Gly Ser Gly Ser Gly Thr Asp
             65                  70
Phe Thr Leu Thr Ile Ser Ser Leu Gln Pro
             75                  80
Glu Asp Val Ala Thr Tyr Tyr Cys Gln Lys
             85                  90
Tyr Asn Ser Ala Leu Leu Thr Phe Gly Gln
             95                 100
Gly Thr Arg Leu Glu Ile Lys Arg Thr Val
            105                 110
Ala Ala Pro Ser Val Phe Ile Phe Pro Pro
            115                 120
Ser Asp Glu Gln Leu Lys Ser Gly Thr Ala
            125                 130
Ser Val Val Cys Leu Leu Asn Asn Phe Tyr
            135                 140
Pro Arg Glu Ala Lys Val Gln Trp Lys Val
            145                 150
Asp Asn Ala Leu Gln Ser Gly Asn Ser Gln
            155                 160
Glu Ser Val Thr Glu Gln Asp Ser Lys Asp
            165                 170
Ser Thr Tyr Ser Leu Ser Ser Thr Leu Thr
            175                 180
Leu Ser Lys Ala Asp Tyr Glu Lys His Lys
            185                 190
Leu Tyr Ala Cys Glu Val Thr His Gln Gly
            195                 200
Leu Ser Ser Pro Val Thr Lys Ser Phe Asn
            205                 210
Arg Gly Glu Cys

<210> SEQ ID NO 16
<211> LENGTH: 647
<212> TYPE: DNA
<213> ORGANISM: Artificial sequence
<220> FEATURE:
<223> OTHER INFORMATION: Light chain m254 antibody

<400> SEQUENCE: 16
ccgacatcca gatgacccag tctccatcct ccctgtctgc                            40
atctgtagga gacagagtca ccatcacttg ccgggcgagt                            80
cagggcatta gcaattattt agcctggtat cagcagaaac                           120
cagggaaagt tcctaagctc ctgatctatg ctgcatccac                           160
tttgcaatca ggggtcccat ctcggttcag tggcagtgga                           200
tctgggacag atttcactct caccatcagc agcctgcagc                           240
```

```
ctgaagatgt tgcaacttat tactgtcaaa agtataacag          280
tgccctcctc accttcggcc aagggacacg actggagatt          320
aaacgaactg tggctgcacc atctgtcttc atcttcccgc          360
catctgatga gcagttgaaa tctggaactg cctctgttgt          400
gtgcctgctg aataacttct atcccagaga ggccaaagta          440
cagtggaagg tggataacgc cctccaatcg ggtaactccc          480
aggagagtgt cacagagcag gacagcaagg acagcaccta          520
cagcctcagc agcaccctga cgctgagcaa agcagactac          560
gagaaacaca aactctacgc ctgcgaagtc acccatcagg          600
gcctgagctc gcccgtcaca aagagcttca acaggggaga          640
gtgttaa                                              647
```

HUMAN MONOCLONAL ANTIBODIES PROTECTIVE AGAINST BUBONIC PLAGUE

This application claims the benefit of priority from an earlier filed provisional application Ser. No. 61/212,166 filed on Apr. 8, 2009, still pending.

This invention was made with government support under contract N01-CO-12400 awarded by National Cancer Institute, and under proposal no. 1.1A0018_07_RD_B awarded by JSTO/DTRA. The government has certain rights in the invention.

INTRODUCTION

Yersinia pestis (Y. pestis) is the causative agent of plague that has killed over an estimated 200 million people in previous pandemics (Perry and Fetherston, 1997, Clin. Microbiol. Rev. 10, 35). The current incident of plague is low but the animal reservoirs for Y. pestis exist worldwide. Sporadic cases have been reported recently with an average case number of 2,500 worldwide (World Health Organization, 2003, Wkly Epidemiol. Rec. 78, 130-135). Y. pestis can be rendered airborne and its potential use as a bioweapon is recognized as a category A agent on the NIAID list of biodefense-related pathogens (Zilinska, R. A., 2006, Crit. Rev. Microbiol. 32, 47-64). Current treatment for plague consists of antibiotics, while a live attenuated vaccine against plague is used in the former Soviet Union for prevention (Titball and Williamson, 2004, Expert. Opin. Biol. Ther. 4, 965-973). Nevertheless, live attenuated whole-cell vaccines or killed whole-cell vaccines have adverse effects to varying degrees (Titball and Williamson, 2004, supra). Though both types of treatment are efficacious, there is a need for an alternative treatment for plague (Casadevall, A., 2002, Emer. Infect. Dis. 8, 833-841). A multiple-antibiotic-resistant isolate of Y. pestis has been isolated, and drug resistance was shown to be mediated by a self-transferable plasmid (Galimand, M. et al., 1997, New Engl. J. Med. 337, 677-680; Welch T. J. et al., 2007, PLoS ONE 2, e309). A subunit vaccine, which consists of two virulent factors, the F1 protein and V-antigen, is currently in human clinical trials (Heath, D. G. et al., 1998, Vaccine 16, 1131-1137; Williamson, E. D. et al., 1995, Fems Immunol. Med. Microbiol. 12, 223-230; Williamson, E. D. et al., 2005, Infect. Immun. 73, 3598-3608). Studies involving the vaccine antigens in various formats have provided the proof-of-concept data that humoral response can be efficient in protection against Y. pestis (Anderson, G. W. et al., 1998, Am. J. Trop. Med. Hyg. 58, 793-799; Williamson, E. D. et al., 1999, Clin. Exper. Immunol. 116, 107-114). There are multiple reports that mouse anti-plague monoclonal antibodies (mAbs) against a Y. pestis challenge can passively protect a mouse against plague (Anderson, G. W. et al., 1997, Am. J. Trop. Med. Hyg. 56, 471-473; Hill, J. et al., 1997, Infect. Immun. 65, 4476-4482; Hill, J. et al., 2003, Infect. Immun. 71, 2234-2238). Therefore, mAb therapy is an attractive alternative to the existing treatments for plague. Despite the promising possibilities, there remains a major hurdle for the use of mouse mAbs for treatment against plague and that is the possible immune response of humans to the mouse mAbs that are currently available. One possibility to ameliorate the immune response against the mouse mAb is to humanize the mAb for use in humans. More preferable, and to avoid antimouse immune reactions altogether, is to develop new and fully human anti-plague monoclonal antibodies for clinical use (Park and Smolen, 2001, Monoclonal Antibody Therapy, In: Scolick M. eds. *Drug Discovery and Designs*. San Diego, Calif., Academic Press, pp 360-420).

We describe here the isolation of three mAbs antibodies from a large naive human phage-displayed Fab phage library. One is against the F1-antigen and the other two are against the V-antigen. When used alone, the human anti-F1 mAb displayed good protective effects, whereas the human anti-V mAbs did not. However, a clear synergistic effect was found when they were used together. Maximum protection by F1 alone could be achieved by altering the antibody administration schedule. This is the first report describing the isolation of fully human anti-plague mAbs that show efficacy in a mouse model of plague. These antibodies represent a significant breakthrough toward adjunctive therapeutic treatment of Y. pestis infection in humans.

SUMMARY OF THE INVENTION

This application describes human monoclonal antibodies against F1 and V antigen of Y. pestis. Fully human antibodies are antibody molecules in which the entire sequence of both the light chain and the heavy chain, including the CDRs, arise from human genes. Individual human monoclonal antibodies specific for F1 antigen, m252, and V antigen, m253 and m254, were produced from a human Fab phage library. The human monoclonal antibodies were protective against Y. pestis bubonic plague challenge when administered prophylactically or therapeutically. (By "prophylactic", it is meant administered before challenge, and by "therapeutic", it is meant administered after challenge.) The anti-F1 antibody protected BALB/c mice from a lethal challenge with Y. pestis CO92 when purified mAb was administered 24 hours before challenge. None of the anti-V mAbs were protective when administered alone. However, surprisingly, protection from Y. pestis challenge was increased when all three human monoclonal antibodies were administered in combination. In fact, the combination of antibodies was effective even when administered up to 2 days after challenge.

The invention provides human monoclonal antibodies recognizing the F1 and V antigen of Y. pestis. Exemplary human antibodies of the invention include, for example, the m252 anti-F1 human monoclonal antibody, the m253 anti-V human monoclonal antibody, and the m254 anti-V human monoclonal antibody. These antibodies have distinct specificities.

For example, human m252 mAb produces a weak-moderate binding signal with peptide 1 (SEQ ID NO:1) and peptide 2 (SEQ ID NO:2) out of 27 peptides which cover the length of the F1-antigen were tested. Both peptides 1 and 2 are located at the N-terminus of the F1-antigen. This suggests that m252 may also recognize a conformational region that involves peptides 1 and 2. The m252 mAb has a heavy chain variable region having the amino acid sequence set forth in SEQ ID NOS:3 and the nucleotide sequence set forth in SEQ ID NO:4. The light chain variable region of m252 has the amino acid sequence set forth in SEQ ID NO:5 and the nucleotide sequence set forth in SEQ ID NO:6.

The binding of human anti-V m253 mAb results in a weak signal with V-antigen peptide 1 (SEQ ID NO:7) and a strong signal with V-antigen peptide 2 (SEQ ID NO:8), near the amino-terminal of the V antigen. m253 mAb has a heavy chain variable region having the amino acid sequence of SEQ ID NOS:9, and the nucleotide sequence set forth in SEQ ID NO:10. m253 light chain variable region has the amino acid sequence set forth in SEQ ID NO:11 and the nucleotide sequence set forth in SEQ ID NO:12.

The binding of human anti-V m254 mAb did not give a specific signal with any of the 53 V-antigen peptides tested, suggesting that the m254 mAb recognizes a conformational region on the V-antigen. Even though m253 and m254 recognize the V antigen of *Y. pestis*, these monoclonals do not compete for the same binding site on the V antigen. m254 mAb has a heavy chain variable region having the amino acid sequence of SEQ ID NOS:13 and a nucleotide sequence set forth in SEQ ID NO:14. The m254 light chain variable region has the amino acid sequence set forth in SEQ ID NO:15 and the nucleotide sequence set forth in SEQ ID NO:16.

The heavy chain complementary determining regions (or CDRs) include an amino acid sequence at least 90%, 92%, 95%, 97% 98%, 99% or more identical to a sequence selected from the group consisting of SEQ ID NO:3, 9, or 13 and a light chain with CDRs that include an amino acid sequence at least 90%, 92%, 95%, 97% 98%, 99% or more identical to a sequence selected from the group consisting of the amino acid sequence of SEQ ID NO:5, 11 or 15.

In an embodiment of the present invention, the antibody of the present invention is an antibody or a functional fragment thereof, which has the variable regions of an antibody described above.

Another embodiment of the invention relates to antibodies that are functionally equivalent to the antibodies listed above. These functionally equivalent antibodies substantially share at least one major functional property with an antibody listed above and herein described comprising: binding specificity to a *Y. pestis* antigen, protection against *Y. pestis* challenge when administered prophylactically or therapeutically, competition for same binding site on *Y. pestis* antigen, and/or use of the same combination of complementarity determining regions. The antibodies can be of any class such as IgG, IgM, or IgA or any subclass such as IgG1, IgG2a, and other subclasses known in the art. Antibodies useful in the present invention also include human antigen-binding antibody fragments of the antibodies of the present invention including, but are not limited to, Fab, Fab' and F(ab')$_2$, Fd, single-chain Fvs (scFv), single-chain antibodies, disulfide-linked Fvs (sdFv). The invention also includes single-domain antibodies comprising either a VL or VH domain. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and a Fc region from different species, or by keeping the complementarity-determining regions and modifying the framework regions to that of another species. Additionally, antibodies included comprise recombinant antibody molecules wherein the variable light chain is chosen from any one of SEQ ID Nos:5, 11, 15, and a variable heavy chain chosen from any one of SEQ ID Nos:3, 9, 13.

A further embodiment of the present invention provides for mixtures of the above-described antibodies, as well as to methods of using individual antibodies, or mixtures thereof for the prevention and/or therapeutic treatment of *Y. pestis* infections in vitro and in vivo, and/or for improved detection of *Y. pestis* infections. Pharmaceutical compositions according to the invention can include one or more antibody of the invention and one or more carrier. These pharmaceutical compositions can be included in kits, such as, for example, diagnostic kits.

Another embodiment relates to the treatment or prevention of *Y. pestis* bacterial infection, or alleviating a symptom associated with such pathologies by administering a therapeutically or prophylactically effective amount of one antibody of the present invention or a mixture of antibodies of the present invention to a subject in need of such treatment. Treatment may include other compositions known to alleviate symptoms or reduce infections, such as antibiotics. The subject to be treated is, e.g., human.

A further embodiment provides passive vaccines for treating or preventing *Y. pestis* bacterial infections comprising a therapeutically or prophylactically effective amount of the antibodies of the present invention which protect against *Y. pestis* infection, in combination with a pharmaceutically acceptable carrier or excipient.

Yet another embodiment provides methods for diagnosis of *Y. pestis* infection by assaying for the presence of *Y. pestis* in a sample using the antibodies of the present invention.

Still another embodiment provides novel immunoprobes and test kits for detection of *Y. pestis* infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to *Y. pestis* to form an immunological complex and detecting the formation of the immunological complex such that presence or absence of the immunological complex correlates with presence or absence of *Y. pestis*.

In another embodiment, there are provided anti-idiotypic antibodies raised against one of the present monoclonal antibodies for use as a vaccine to elicit an active anti-F1 or anti-V antigen response.

In a further embodiment, there are provided antigenic epitopes as a component of a *Y. pestis* vaccine. For example, the epitopes described above comprising SEQ ID NO:1, 2, or 8, or conservative changes thereof which are still recognized by the antibodies, are useful for actively immunizing a host to elicit production of protective antibodies against *Y. pestis*.

BRIEF DESCRIPTION OF THE DRAWINGS

These and other features, aspects, and advantages of the present invention will become better understood with reference to the following description and appended claims, and accompanying drawings where:

PBS indicates m253 mixed with equal volume of PBS buffer only. In all panels, NC indicates samples with no primary antibodies added serving as secondary antibody controls.

Figure 3A:
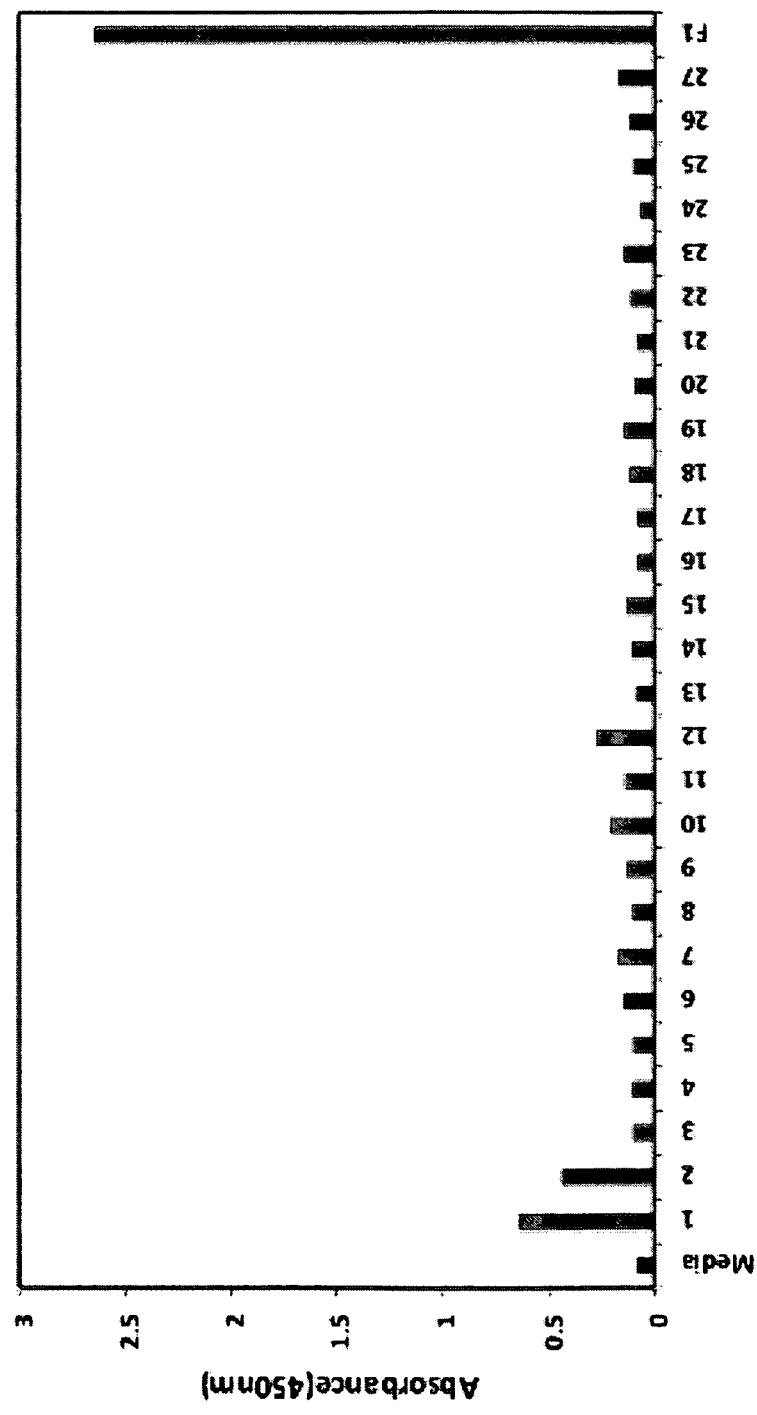

FIGS. 3a, 3b, and 3c. Epitope mapping of the human anti-F1 and anti-V antibodies by peptide binding assay. 3a. Each of twenty-seven peptides that covered the full length of the F1-antigen were used to coat an ELISA plate, and binding by the human anti-F1 m252 antibody was analyzed. The sample labeled F1 was the full-length antigen used to coat the plate as the positive control, and the sample labeled Media was the negative control with no primary antibody added. 3b and c. Each of fifty-two peptides that covered the full length of the V-antigen was used to coat an ELISA plate, and the human anti-V m253 (b) and m254 (c) mAbs were used, respectively, to analyze for the binding. The sample labeled V was the positive control, and the sample labeled Media was the negative control without the primary antibody.

Figure 4:
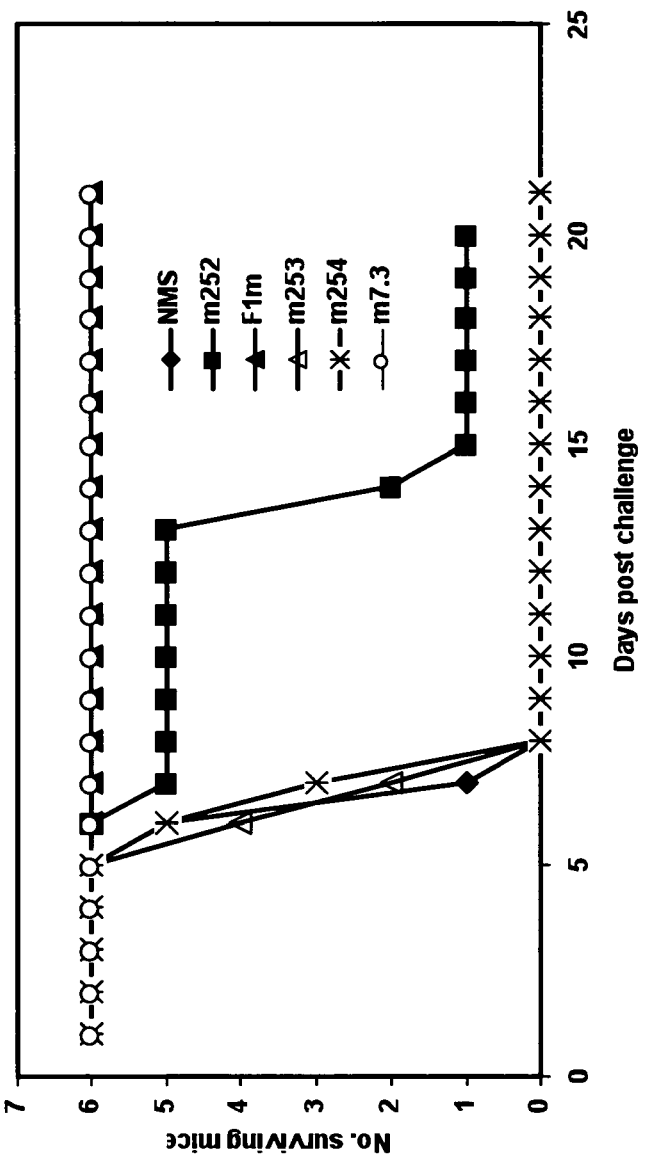

FIG. 4. The human anti-F1 m252 IgG extended the mean-time-to-death (MTD) in a *Y. pestis* mouse model of plague. Antibodies were administered i.p. 24 hrs before challenge. The number of surviving mice for each treatment group was monitored for at least 21 days after challenge. The following antibodies were used: normal mouse serum (NMS); human anti-F1 (m252); mouse anti-F1 (F1m); human anti-V (m253); human anti-V (m254); and mouse anti-V (m7.3).

Figure 5:
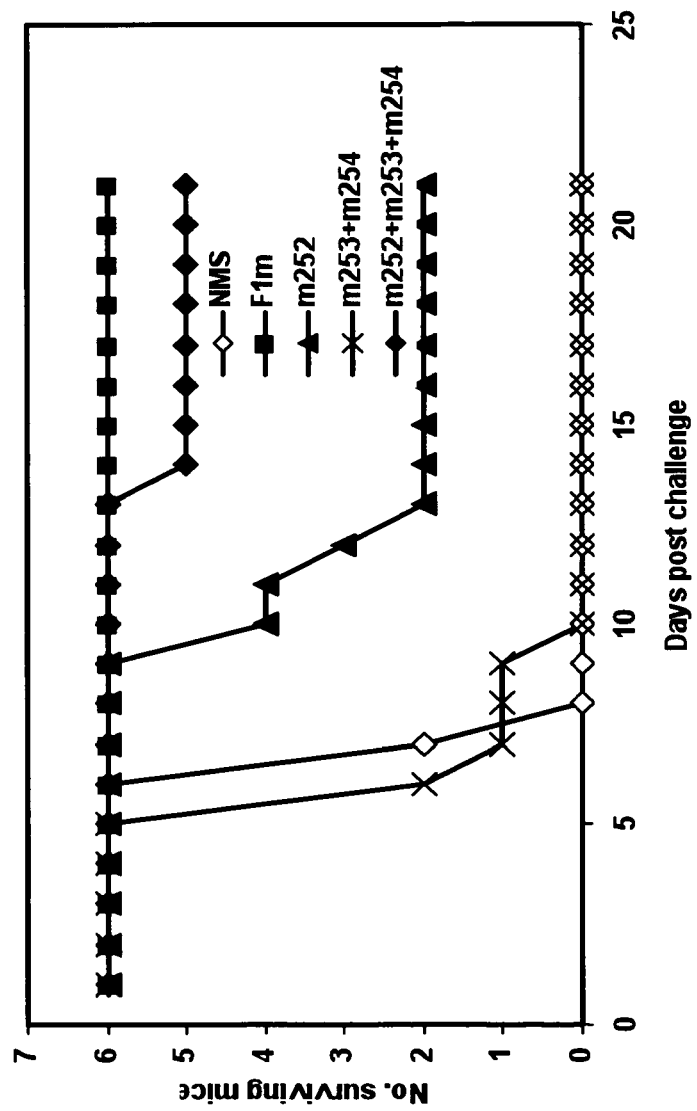

FIG. 5. Synergistic effect between the human anti-F1 and human anti-V IgGs in protection against a *Y. pestis* challenge. Human anti-F1 and anti-V mAbs were used either individually or in combinations as indicated and administered to mice i.p. 24 hrs prior to the *Y. pestis* challenge. Mice were monitored for at least 21 days after challenge. The mouse anti-F1 F1m mAb was used as a control in the study.

Figure 6B:
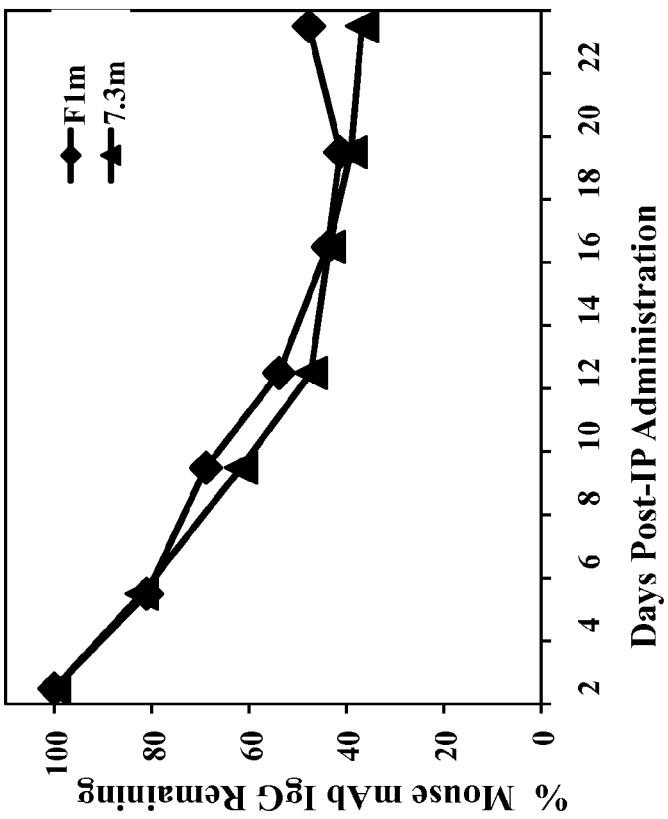
Figure 6A:
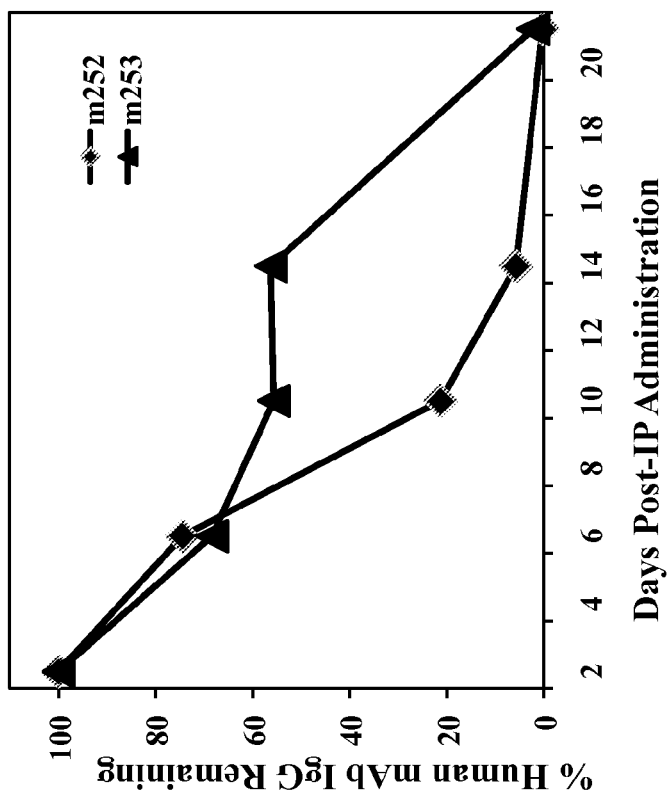

FIGS. 6A and 6B. Serum concentrations of human and mouse anti-F1 and anti-V mAbs in the plague mouse model over time. The same amount of human IgGs (500 ug) as used in the challenge studies was administered via i.p. and blood samples were collected at indicated time points. The human IgG concentration was determined by ELISA. The data shown are averages from three mice for each IgG. A. The amount of remaining human anti-F1 m252 and anti-V m254 in mouse serum. B. The amount of remaining mouse anti-F1 F1m and anti-V 7.3m in mouse serum.

Figure 7:
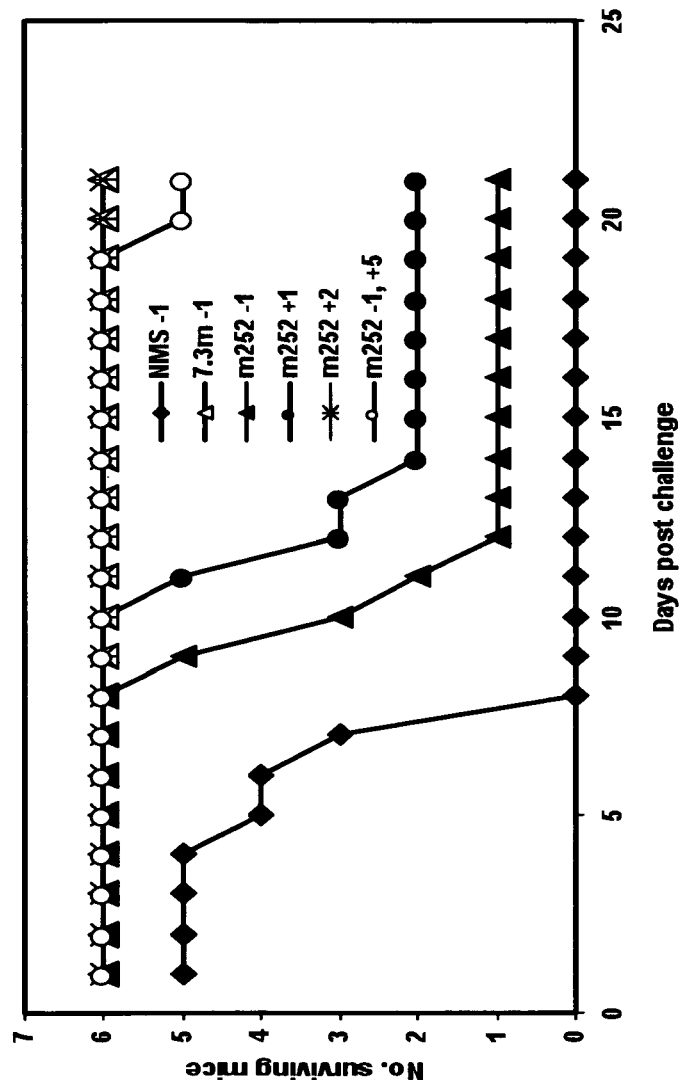

FIG. 7. Post-challenge administration of the human anti-F1 m252 mAb conferred better protection. The human anti-F1 m252 mAb was administered before or after *Y. pestis* challenge, and mice were monitored for 21 days after challenge. The mouse anti-V 7.3m mAb was used as a control mAb. Normal mouse serum (NMS) was used as a negative control and had only 5 mice per group. The numbers behind each antibody represent the time in days in which the antibody was administered to mice relative to the day of challenge (day 0). The two numbers after the human anti-F1 m252 (−1 and +5) represent two different days when the mAb (500 ug) was added to the same group of mice relative to the day of challenge.

DETAILED DESCRIPTION

In the description that follows, a number of terms used in recombinant DNA and immunology are extensively utilized. In order to provide a clearer and consistent understanding of the specification and claims, including the scope to be given such terms, the following definitions are provided.

The term "antibody" is art-recognized terminology and is intended to include molecules or active fragments of molecules that bind to known antigens. Examples of active fragments of molecules that bind to known antigens include Fab and F(ab')$_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011-1019 (1982). The term "antibody" also includes bispecific and chimeric antibodies.

The language "monoclonal antibody" is art-recognized terminology. The immunogen (antigen) of interest is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (replicon vector, vaccinia), or as DNA, or as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen is removed and splenocytes are extracted and fused with myeloma cells using the well-known processes of Kohler and Milstein (*Nature* 256: 495-497 (1975)) and Harlow and Lane (*Antibodies: A Laboratory Manual* (Cold Spring Harbor Laboratory, New York 1988)). The resulting hybrid cells are then cloned in the conventional manner, e.g. using limiting dilution, and the resulting clones, which produce the desired monoclonal antibodies, cultured.

Herein the monoclonals were produced by "sequential antigen panning" which refers to a method of producing an antibody or antibodies comprising isolating the antibody or antibodies by screening a phage display library for antibodies that can bind to an antigen, wherein the isolation is continued by screening the binding antibodies for the ability to bind the antigen at a lower concentration or to bind an additional antigen, wherein this process can continue for two or more cycles, wherein the antibody or antibodies that bind on the last cycle are selected.

A variety of methods exist in the art for the production of monoclonal antibodies. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains of a desired species in place of the homologous human sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The term "epitope" is art-recognized. It is generally understood by those of skill in the art to refer to the region of an antigen or antigens that interacts with an antibody. An epitope of a peptide or protein antigen can be linear or conformational, or can be formed by contiguous or noncontinguous amino acid sequences of the antigen. The F1 and V antigens, like many proteins, contain many epitopes. The epitopes or peptides recognized by the antibodies of the present invention and conservative substitutions of these peptides which are still recognized by the antibody are an embodiment of the present invention. These peptides offer a convenient method for eluting V antigen to mAb on immunoaffinity columns. For example, when an antibody which recognizes the epitope for m253 is used in an immunoaffinity column to purify V antigen, the peptide recognized by the antibody can be added to the immunoaffinity column to elute the V antigen. Further truncation of these epitopes may be possible since antigenic epitopes have been reported to be represented by as few as five amino acid residues.

The nucleotide and amino acid sequence of the heavy and light chain variable regions of the mAbs of the invention are described in this application. The invention further provides polynucleotides comprising a nucleotide sequence encoding an antibody of the invention and fragments thereof. The invention also encompasses polynucleotides that hybridize under stringent or lower stringency hybridization conditions to polynucleotides that encode an antibody of the present invention.

The polynucleotides may now be obtained by any method known in the art. For example, since the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Since the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

A vector comprising any of the above-described isolated or purified nucleic acid molecules, or fragments thereof, is further provided by the present invention. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, plasmid, phage, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. For example, a cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI110, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or normative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Optionally, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, e.g., Gateway™ (Invitrogen)). See, also, U.S. Pat. No. 5,314,995.

In view of the foregoing, the present invention also provides a composition comprising an above-described isolated or purified nucleic acid molecule, optionally in the form of a vector. The composition can comprise other components as described further herein.

Also in view of the above, the present invention provides a host cell comprising an above-described isolated or purified nucleic acid molecule, optionally in the form of a vector. It is most preferable that the cell of the present invention expresses the vector, such that the oligonucleotide, or fragment thereof, is both transcribed and translated efficiently by the cell. Examples of cells include, but are not limited to, a human cell, a human cell line, E. coli (e.g., E. coli TB-1, TG-2, DH5α, XL-Blue MRF' (Stratagene), SA2821 and Y1090), B. subtilis, P. aerugenosa, S. cerevisiae, N. crassa, insect cells (e.g., Sf9, Ea4) and others set forth herein below. The host cell can be present in a host, which can be an animal, such as a mammal, in particular a human.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 3, 9, 13, and the light chain immunoglobulin molecules represented in SEQ ID NOS: 5, 11, 15, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Fully human antibodies are described in this application. Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies produced using other techniques but retaining the variable regions of the mAb of the present invention are part of this invention. Human antibodies can also be produced using transgenic mice which are incapable of expressing functional endogenous mouse immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human mAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

The antibodies of the present invention may be monospecific, bispecific, trispecific or of greater multispecificity. Multispecific antibodies may be specific for different epitopes of V or F1 antigen or may be specific for an antigen as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Bispecific antibodies are monoclonal antibodies that have binding specificities for at least two different antigens. In the present invention, one of the binding specificities may be directed towards F1-antigen, the other may be for any other *Y. pestis* antigen, or for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

Further included in the present invention are antibodies that bind to the same epitope as the antibodies of the present invention. Epitope mapping studies described in this application show that m252 recognizes an epitope on F1 antigen consisting of a 17 amino acids peptide (SEQ ID NO:1) and a 23 amino acid peptide (SEQ ID NO:2), and that m253 recognizes an epitope on V antigen consisting of a 17 amino acids peptide (SEQ ID NO:7) and a 22 amino acid peptide (SEQ ID NO:8). Data indicate that m253 has weak binding to SEQ ID NO:7 but very strong binding to SEQ ID NO:8, indicating that the peptide identified as SEQ ID NO:8 is the primary epitope and the peptide identified as SEQ ID NO:7 is the secondary epitope. Antibodies which compete with m252, m253 or m254 are considered to recognize the epitope of each respective antibody and are considered equivalent to the antibodies of the present invention. Assays for determining whether or not an antibody competes with an antibody of the present invention are known to a person with ordinary skill in the art and are described below.

To determine if an antibody can compete for binding to the same epitope as the epitope bound by the antibodies of the present invention including the antibodies produced by the hybridomas deposited with the ATCC, a cross-blocking assay, e.g., a competitive ELISA assay, can be performed. In an exemplary competitive ELISA assay, antigen coated on the wells of a microtiter plate is pre-incubated with or without candidate competing antibody and then the biotin-labeled anti-F1 or anti-V antibody of the invention is added. The amount of labeled antibody bound to the antigen in the wells is measured using avidin-peroxidase conjugate and appropriate substrate. The antibody can be labeled with a radioactive or fluorescent label or some other detectable and measurable label. The amount of labeled antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an antibody of the invention if the candidate antibody can block binding of the antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

By further mapping of the binding site of the monoclonal antibodies described in this application other peptides useful as a vaccine or a therapeutic can be predicted. Therefore, in another aspect, this invention relates to a method for identifying protective antigenic epitopes as described in the Examples below. Other methods are known in the art and include a method comprising (i) reacting a monoclonal antibody described in this application to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine, for example.

The epitopes or peptides to which the monoclonal antibodies of the present invention bind can constitute all or part of an eventual active vaccine candidate. An active vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

The present invention also pertains to hybridomas producing antibodies which bind to an epitope of V antigen or an epitope of F1-antigen. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above for a more detailed description of the method of fusion.

The present invention still further pertains to a method for detecting *Y. pestis* V antigen or *Y. pestis* F1-antigen in a sample suspected of containing *Y. pestis* either or both antigens. The method includes contacting the sample with an antibody which binds an epitope of the antigen, allowing the antibody to bind to theantigen to form an immunological complex, detecting the formation of the immunological complex and correlating the presence or absence of the immunological complex with the presence or absence of the antigen in the sample. The sample can be biological, environmental or a food sample.

The language "detecting the formation of the immunological complex" is intended to include discovery of the presence or absence of *Y. pestis* antigen in a sample. The presence or absence of *Y. pestis* antigen can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555-612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a *Y. pestis* vaccinee and a monoclonal antibody of the present invention, are allowed to compete for binding of the antigen. The amount of monoclonal bound is then measured, and a determination is made as to whether the serum contains anti V antigen antibodies. This competitive ELISA can be used to indicate immunity to known protective epitopes in a vaccinee following vaccination and to identify competing antibodies.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1-31), and Schurs, A. H. W. M., et al. 1977 (*Clin. Chim Acta* 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, biological fluid, or a solution for administering to a subject, such as a vaccine, or immunoglobulin. By "environmental sample" is meant a sample such as soil and water. Food samples include canned goods, meats, and others.

Yet another aspect of the present invention is a kit for detecting V antigen or F1 antigen or both in a biological sample. The kit includes a container holding one or more antibodies which binds an epitope of V antigen or F1-antigen and instructions for using the antibody for the purpose of binding to the antigen to form an immunological complex and detecting the formation of the immunological complex such that the presence or absence of the immunological complex correlates with presence or absence of the antigen in the sample. Examples of containers include multiwell plates which allow simultaneous detection of V antigen in multiple samples.

As described in greater detail in the Examples, the present inventors have isolated three human monoclonal antibodies which bind to epitopes on F1 antigen and V antigen and display in vitro and/or in vivo protective properties. Significantly, the reactivity of the mAbs is applicable against a broad variety of different wild type and laboratory *Y. pestis* strains of different types as determined in vitro using ELISA, western blot, radioimmunoprecipitation; or in vivo against challenge with *Y. pestis*. Wild type strains include for example Angola, Antigua, Harbin 35, Pestoides A, Pestoids B, Pestoids C, Pestoides D, Pestoides Aa, Pestoides Ba, Pestoides F, Pestoides G, Pestoides J, CO92, KIM, Nicholisk 41, 195P, Indian isolate 111, EV76, Java 9, La Paz, Russian vaccine strain, Stavropol, 684, 538, 7752, Alexander, Dobson, Shasta, 242, A12, 564, 1171, South Park, and Yreka. Laboratory strains can be derived from wild type strains and include those which have been adapted, and those derived by site-directed mutagenesis such as various CO92 derivatives including CO92 Pgm-, CO92 Lcr-, CO92 pPst, C12, and others.

Given these results, monoclonal antibodies according to the present invention are suitable both as therapeutic and prophylactic agents for treating or preventing *Y. pestis* infection in susceptible plague-infected subjects. Subjects include rodents such as mice or guinea pigs, non-human primates, and other mammals, including humans.

In general, this will comprise administering a therapeutically or prophylactically effective amount of one or more monoclonal antibodies of the present invention to a susceptible subject or one exhibiting plague infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, corn, potato, banana or strawberry. Methods for the production of antibodies in these systems are known to a person with ordinary skill in the art. Preferably, the antibodies used are compatible with the recipient species such that the immune response to the mAbs does not result in clearance of the mAbs before bacteria can be controlled, and the induced immune response to the mAbs in the subject does not induce "serum sickness" in the subject. Preferably, the mAbs administered exhibit some secondary functions such as binding to Fc receptors of the subject.

Treatment of individuals having *Y. pestis* infection may comprise the administration of a therapeutically effective amount of one or more of the above nucleic acid molecules, vectors, host cells, antibodies, fusion proteins, conjugates, and in particular monoclonal antibodies of the present invention with or without antibiotics. The above nucleic acid molecules, vectors, host cells, antibodies, fusion proteins and conjugates can be administered to a human or a collection of cells by injection (e.g., transdermal, intravenous, intraperitoneal, subcutaneous, intramuscular), or by other methods, such as infusion, that ensure delivery to the bloodstream in an effective form. Local or intravenous injection is preferred. Other methods include topical, such as topical intranasal administration or administration by inhalant, vaginal, rectal, ophthalmic, oral, intravenous drop, subcutaneous, and the like.

As used herein, "topical intranasal administration" means delivery of the compositions into the nose and nasal passages through one or both of the nares and can comprise delivery by a spraying mechanism or droplet mechanism, or through aerosolization. Delivery also can be directly to any area of the respiratory system (e.g., lungs) via intubation.

The antibodies can be provided in a kit as described below. The antibodies can be used or administered as a mixture, for example in equal amounts, or individually, provided in sequence, or administered all at once. In providing a patient with antibodies, or fragments thereof, capable of binding to F1 or V antigen, or an antibody capable of protecting against plague in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another therapeutic use of the monoclonal antibodies of the present invention is the active immunization of a patient using an anti-idiotypic antibody raised against one or more of the present monoclonal antibodies. Immunization with an anti-idiotype which mimics the structure of the epitope could elicit an active *Y. pestis* antigen response (Linthicum, D. S. and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide, with or without adjuvant, in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against *Y. pestis* are intended to be provided to recipient subjects in an amount sufficient to effect a reduction in the *Y. pestis* infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly (lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the compositions disclosed herein may be carried out by any suitable means, including intravenous, parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestible liquid or solid formulation. Formulations for topical administration may include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable. Some of the compositions potentially can be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, and potassium hydroxide, and organic bases, such as mono-, di-, trialkyl and aryl amines and substituted ethanolamines.

Effective dosages and schedules for administering the above nucleic acid molecules, vectors, host cells, antibodies, and fusion proteins can be determined empirically, and making such determinations is within the skill in the art. Those skilled in the art will understand that the dosage that must be administered will vary depending on, for example, the subject, the route of administration, whether a nucleic acid molecule, vector, host cell, antibody, fusion protein or conjugate is being administered, and whether other drugs being administered, not to mention the age, condition, and gender of the human and the extent of disease. Guidance in selecting appropriate doses for antibodies (or fusion proteins comprising same) is found in the literature on therapeutic uses of antibodies, e.g., Handbook of Monoclonal Antibodies, Ferrone et al., eds., Noges Publications, Park Ridge, N.J. (1985), Ch. 22 and pp. 303-357; Smith et al., Antibodies in Human Diagnosis and Therapy, Haber et al., eds., Raven Press, New York (1977), pp. 365-389. Nucleic acids, vectors and host cells should be administered so as to result in comparable levels of production of antibodies or fusion proteins thereof.

Following administration of a nucleic acid molecule, vector, host cell, antibody, fusion protein or conjugate for treating, inhibiting, or reducing the severity of an *Y. pestis* infection, the efficacy of the therapeutic agent can be assessed in various ways well-known to the skilled practitioner. For instance, one of ordinary skill in the art will understand that an antibody of the invention is efficacious in treating or inhibiting an *Y. pestis* infection in a subject by observing that the antibody reduces bacterial load or prevents a further increase in bacterial load. Bacterial loads can be measured by methods that are known in the art, for example, using polymerase chain reaction assays to detect the presence of *Y. pestis* nucleic acid or antibody assays to detect the presence of *Y. pestis* protein in a sample (e.g., but not limited to, blood) from a subject or patient, or by measuring the level of circulating anti-*Y. pestis* antibody levels in the patient.

The nucleic acid molecules, vectors, host cells, antibodies, fusion proteins and/or conjugates of the invention can be administered prophylactically to patients or subjects who are at risk for being exposed to *Y. pestis* or who have been newly exposed to *Y. pestis*. In subjects who have been newly exposed to *Y. pestis* but who have not yet displayed the presence of the bacteria (as measured by PCR or other assays for detecting the bacteria) in blood or other body fluid, efficacious treatment with an antibody of the invention partially or completely inhibits the appearance of the bacteria in the blood or other body fluid.

The nucleic acid molecules, vectors, host cells, antibodies, fusion proteins and/or conjugates of the invention can be combined with other well-known therapies and prophylactic vaccines already in use. Such combinations can generate an additive or a synergistic effect with current treatments. The nucleic acid molecules, vectors, host cells, antibodies and/or conjugates of the invention can be combined with *Y. pestis* therapies and vaccines such as antibiotics. Such therapies can be administered in the manner already in use for the known treatment providing a therapeutic or prophylactic effect.

As described above, the compositions can be administered in a pharmaceutically acceptable carrier and can be delivered to the subject's cells in vivo and/or ex vivo by a variety of mechanisms well-known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well-known in the art. Compositions comprising a nucleic acid, optionally in the form of a vector encoding the antibody or fusion protein comprising same, can be introduced into the cells via any gene transfer mechanism, such as, for example, calcium phosphate mediated gene delivery, electroporation, microinjection or proteoliposomes. The transduced cells then can be infused (e.g., in a pharmaceutically acceptable carrier) or homotopically transplanted back into the subject per standard methods for the cell or tissue type. Standard methods are known for transplantation or infusion of various cells into a subject.

Thus, in view of the above, the present invention provides a method of inhibiting an infection of a human at risk of becoming infected with Y. pestis. The method comprises administering to the human an infection-inhibiting amount of an above-described nucleic acid, vector, host cell, antibody or fusion protein, whereupon the infection of the human is inhibited. Preferably, the infection is inhibited to such a degree that the human does not evidence the signs and symptoms of infection.

Also in view of the above, the present invention provides a method of reducing the severity of an infection of a human infected with Y. pestis. The method comprises administering to the human a severity of infection-reducing amount of an above-described nucleic acid, vector, host cell, antibody or fusion protein, whereupon the severity of the infection of the human is reduced. Preferably, the reduction in the severity of infection is to such a degree that the human does not evidence the signs and symptoms of infection, or preferably the human does not experience an increase in the severity of disease.

The treatment may be given in a single dose schedule, or preferably a multiple dose schedule in which a primary course of treatment may be with 1-10 separate doses, followed by other doses given at subsequent time intervals required to maintain and or reinforce the response, for example, at 24 hours, 48 hours, 1-4 months for a second dose, and if needed, a subsequent dose(s) after several months. The treatment can include treatment with antibiotics in addition to the antibodies of the invention. Examples of suitable treatment schedules include: (i) −1 day for prophylactic treatment, (ii) 0, +1 day, and +2 days relative to time of infection for therapeutic treatment (ii) 0 through 30 days, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Materials and Methods

Bacterial strains and cultivation. The Y. pestis CO92 strain used in the challenge studies was originally obtained from T. Quan, Centers for Disease Control and Prevention, Fort Collins, Co. It was isolated from the sputum of a human case of pneumonic plague (Doll, J. M. et al., 1994, Am. J. Trop. Med. Hyg. 51, 109-114). The Y. pestis CO92 was grown and inoculum prepared for challenges essentially as described previously (Anderson, G. w. et al., 1996, Infect. Immun. 64, 4580-4585). A Y. pestis pgm-strain, which was originally isolated from Y. pestis CO92, and used in the antibody binding studies described below was obtained from Susan L. Welkos (US-AMRIID, Frederick, Md.)

Proteins and peptides. Y. pestis purified F1, V, and F1-V (Powell, B. S., et al., 2005, Biotechnol. Prog. 21, 1490-1510) protein antigens were obtained from Brad Powell (USAMRIID, Fort Detrick, Frederick, Md.). The 27-peptide array that covered the F1-antigen were 14- to 17-mers with 11 amino acid overlaps; they were obtained from the Biodefense and Emerging Infections Research Resources Repository (BEI) (Manassas, Va.). The 53-peptide array that covered the V-antigen were 15- to 17-mers with 11 or 12 amino acid overlaps and were obtained from BEI.

Mouse monoclonal antibodies. The anti-F1 mouse Mab F1-04-A-G1 (or mF1) was provided by George Anderson (USAMRIID) (Anderson, G. W. et al., 1997, supra), and anti-V mouse Mabs 10-1, 74-1, 84-1, and 141-1 as well as the control IgG1 mouse anti-*Burkholderia mallei* (Bm) antibody were obtained from Sylvia Trevino (USAMRIID) and anti-V mouse Mab 7.3 was obtained from Jim Hill (Porton Down, Wiltshire, UK) (Hill, J. et al., 1997, Infect. Immun. 65, 4476-4482) and used in competition ELISAs and as positive controls in mouse passive protection experiments. All mice Mabs were IgG1 isotypes.

Selection of anti-F1 and V Fabs. Purified F1- and V-proteins were either coated directly to Maxisorp plates (Nunc, Denmark) in PBS buffer at 4° C., overnight for plate format panning or were biotin-labeled first with EZ-link Sulfo-NHS-LC-Biotin (Pierce, Rockford, Ill.) for streptavidin-conjugated magnetic bead format panning. The labeling was performed according to the manufacture's recommended protocol. For the plate format, approximately $10^{12}$ Fabs displayed on the surface of phage amplified from a large naive library (Zhu, Z. et al., 2007, Proc. Natl. Acad. Sci. U.S.A. 104, 12123-12128) were suspended in PBS with 2% dry milk and applied to wells coated with the F1- or V-proteins. After incubating for 2 hours at room temperature, each well was washed 5 times for the first round and 10 times for the subsequent rounds before the phage were rescued with TG1 cells at the exponential growth phase. For the bead format, biotin-labeled F1- and V-antigens were first incubated with the same amount of phage as in the plate format in 1 ml of PBS+2% dry milk suspension at room temperature for 2 hour. Fifteen µl of Dynabeads MyOne Streptavidin T1 (Invitrogen Dynal AS, Oslo, Norway) pre-blocked with PBS+2% dry milk was then added to the antigen/phage mixture for one hour at room temperature. The beads were then washed 5 times with PBS for the first round and 10 times for the subsequent rounds.

Phage were then rescued with TG1 cells. A total of four rounds were performed for each antigen with each format. Monoclonal ELISA was then performed to select for positive clones. One hundred clones were screened for each antigen from each format. Only clones displaying an OD405>2.0 were selected for plasmid preparation and sequencing.

Expression, purification, conversion to IgG1, and generation of stable clones. Clones selected as described above were transformed into *E. coli* strain HB2151 for expression (Burton, D. R. 2001, Overview: amplification of antibody genes. In: Barbas, C. F. et al., Eds., *Phage display: a laboratory manual.* Cold Spring Harbor, N.Y., N.Y., Cold Spring Harbor Laboratory Press). Briefly, a single clone was inoculated into 2YT supplemented with 100 units of ampicillin and 0.2% glucose and incubated at 37° C. with shaking. When the OD600 reached 0.6-0.9, IPTG was added to achieve a final concentration of 1 mM and the culture was shifted to 30° C. with shaking and incubated overnight. Cells were then collected, and lysed with polymyxin B (Sigma, St Louis) in PBS, and mixture subjected to Ni-NTA agarose bead (Qiagen, Hilden, Germany) purification. For IgG1 production, the heavy and light chains of the respective Fabs were cloned into the bi-cistronic expression vector pDR12 kindly provided by Dennis Burton (Scripps Research Institute, La Jolla, Calif.). For small scale IgG1 production, transient transfection and expression in Freestyle HEK 293F cells (Invitrogen, Carlsbad, Calif.) were used. For large scale production, stable clones were generated using CHO-K1 (ATCC, Manassas, Va.) cells. Briefly, the heavy and light chains of the three human anti-plague IgG1s were cloned into pDR12 vectors and transfected into CHO-K1 cells. One day after transfection, the cells were re-plated and subjected to selection in GMEM medium supplemented with 25 µM MSX. Two weeks later, the MSX resistant clones were amplified further. The clones were tested for the expression of respective IgG1s and then adapted to growth in serum-free medium HyQSFM4-CHO (HyClone, Logan, Utah) supplemented with 30 µM MSX. The serum-free growth medium was then collected and passed through a protein A-sepharose resin column for IgG1 purification.

Characterization of the binding by the human anti-F1 and anti-V Fabs and IgGs. An ELISA assay was used to assess the binding ability of the Fabs and IgG1s. Briefly, F1- and V-antigens were coated to a Costar high binding small well 96-well plate (Corning, Corning, N.Y.) and incubated overnight at 4° C. The next day, the plate was blocked with 2% dry milk in PBS before serial dilution of Fabs or IgGs were applied to the plate. After an incubation of the plate at 37° C. for one hour, anti-His-horse radish peroxidase (HRP) for Fab detection or anti-human-Fc-HRP (for IgG detection) in PBS+ 2% dry milk was added to each plate and incubated for another hour at 37° C. The plates were then washed four times, and the ABTS substrate (Roche, Mannheim, Germany) was added. After approximately 10 min at room temperature, the OD405 was taken.

For competition studies between the mouse Mabs and human Fabs the antigen at 2 ug/ml (F1-protein or V-antigen) was used to coat 96-well plates (Immulon 2HB, Thermo Electron, Milford, Mass.), and the plates were incubated overnight at 4° C. After washing the plates, a blocking solution (1% bovine serum albumin with 0.05% Tween 20 in PBS) was added to the plates, and plates incubated for 1 hr at 37° C. The flag-labeled human Fabs, and biotinylated-mouse Mab were allowed to bind to the antigen simultaneously for 1 hr at 37° C. To detect the presence of the human Fab, an anti-flag-M2-peroxidase conjugate was used, and to detect the amount of biotinylated mouse Mab present, a streptavidin-conjugated HRP was added for 1 hr at 37° C., before adding a hydrogen peroxidase-3,3',5,5'-tetramethylbenzidine solution. The color reaction was allowed to develop at room temperature for 15 min and read at 450 nm.

For analysis of IgG1 binding to F1- or V-antigen peptides, the peptides were added to the plates in 0.05 ml per well at 25 μg/ml. and the plates incubated overnight at 4° C. in Immunlon 2HB 96-well plates. After the washing and blocking steps as described above, binding of the human and mouse mAbs IgGs was detected as described above. The binding of all mAbs to the peptides was evaluated at 10 μg/ml.

Flow cytometry and immunofluorescence analysis of IgG binding to bacterial cells. Flow cytometry was used to analyze the binding of the human anti-F1 and anti-V antigen IgG1s to *Y. pestis* pst-whole-cells. *Y. pestis* pgm− was first streaked onto a sheep-blood agar plate and grown at room temperature (RT) for 3 to 4 days until colonies were readily visible. A single colony was picked and inoculated into 10 ml of Heart Infusion Broth (Remel, Lenexa, Kans.) containing 02% xylose and 2.5 mM $CaCl_2$, and cells grown overnight (o/n) at RT with rigorous shaking. The next day, an aliquot of the bacteria culture was shifted to 37° C., and the other remained at RT, and the cultures were allowed to continue for another 3 hours before the bacteria were collected and suspended in PBS. Ten μL of bacterial cells was mixed with 90 μL of Fc Block solution [PBS with 1% FCS and 10 ug/ml FcBlock (BD Bioscience)] to achieve a final density of $1\times10^7$ cells/ml. Human or mouse IgGs were added to the bacterial cell suspension to a final concentration of 10 μg/ml. After incubating at 4° C. for 30 min, the bacterial cells were collect by centrifugation and suspended in 1 ml of PBS, and cells washed twice. The bacterial cells were then suspended in the same Fc Block solution, and secondary antibodies, which included either goat anti-mouse IgG-FITC (Pierce, Rockford, Ill.) or goat anti-human IgG-FITC (Southern Biotech, Birmingham, Ala.) were added to the cells at a dilution of 1:100. After 30 min at 4° C., the cells were then washed three times with PBS and subjected immediately to FACS analysis using a FACS-caliber (BD Bioscience, San Diego, Calif.), after the cells were fixed with 4% paraformaldehyde. For detection of antibody binding to whole-cells by immunofluorescent microscopy, the growth of *Y. pestis* pgm− and the sample preparation for binding by human or mouse anti-F1 or anti-V mAbs was identical as that for the FACS analysis, except a Nikon T-2000 fluorescent microscope (Nikon Instruments Inc., Melville, N.Y.) was used for detection.

Passive protection by human or mouse anti-F1 or anti-V mAbs and *Y. pestis* challenge studies. Antibodies to be evaluated for their efficacy against a plague challenge were given intraperitoneal (500 μg per mouse, except when stated differently in the figure legend) to 6-10 week old BALB/c mice 24 h before they were challenged or at time points post-challenge as indicated in the figure legend. The challenge dose was prepared from frozen stocks of *Y. pestis* CO92 that were streaked on tryptose blood agar slants and incubated at 28° C. for 48 h. After the incubation period, the slants were rinsed with 10 mM potassium phosphate buffer, pH 7.0, and cell density adjusted to the required density with the same buffer. Mice were given the challenge dose of $LD_{50}$~25-40, subcutaneously in 0.2 ml, where $1LD_{50}$ is equal to 1.9 cfu (Welkos, S. L. et al., 1995, Contrib. Microbiol. Immunol. 13, 299-305) and observed for at least 21 days.

Research was conducted in compliance with the Animal Welfare Act and other federal statues and regulations relating to animals and experiments involving animals and adheres to principles stated in the *Guide for the Care and Use of Labo-* ratory Animals, National Research Council, 1996. The facility where this research was conducted is fully accredited by the Association for Assessment and Accreditation of Laboratory Animal Care International.

Half-life of human or mouse anti-F1 and anti-V mAbs given passively to mice. An ELISA as described above was used to detect the amount of human or mouse anti-F1 and anti-V mAbs present in mice over time. Briefly, F1-V protein (2 μg/ml in 0.2 M carbonate buffer, pH 9.4)) was used to coat a 96-well plate (Immulon 2HB) overnight at 4° C. before washing and blocking. Two-fold dilutions of mouse serum taken retro-orbitally after ip administration of the mAb were made in 1×PBS with 1% BSA and 0.05% tween-20, added to plates and incubated for 1 hr at 37° C. before washing. The amount of human or mouse anti-F1 or anti-V mAb binding to the antigens was detected by the addition of goat-anti-human or goat-anti-mouse IgG conjugated to HRP (Southern Biotechnology). The results from 3 mice at each time point for each mAb was performed in triplicate and were reported as the mean of the reciprocal of the highest dilution giving a mean OD of at least 0.1, which is at least twice the standard deviation (SD).

Example 1

Selection and Purification of Human Anti-F1 and Anti-V Fabs Clones

Figure 1:
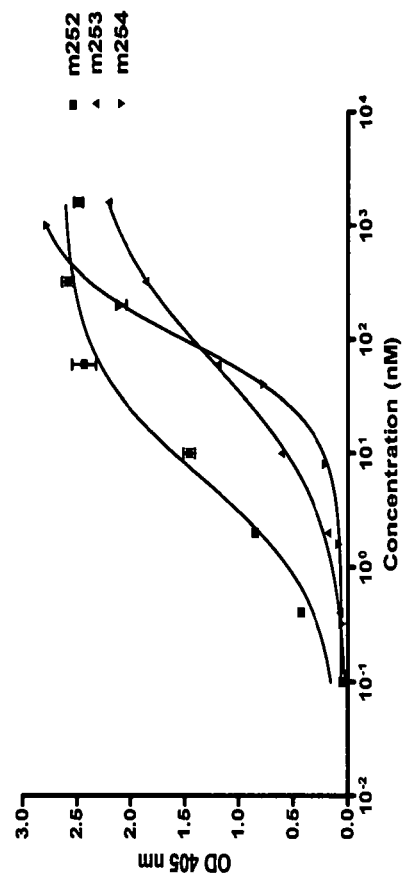
FIGS. 1a, 1b, 1c, and 1d. Characterization of the anti-F1 and anti-V antigen human antibodies. a. Anti-F1 human antibody m252 and anti-V human antibodies m253 and m254 were expressed as Fab fragments, purified, and analyzed on a reducing SDS-PAGE gel. b. Specific binding by the Fab antibody fragments to their respective antigens in an ELISA assay. c. The three human anti-F1 and anti-V antibodies were expressed as IgG1s, purified and analyzed on a reducing SDS-PAGE gel. d. Specific binding of the purified IgG1s to their respective antigens in an ELISA assay.
Figure 1:
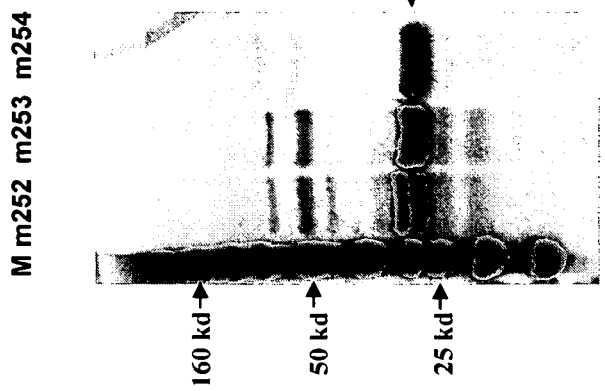

With the F1 antigen, only the plate format yielded positive Fab clones. Sequencing of the clones confirmed that they were identical and designated as m252. With the V-antigen, the plate and bead format each yielded two positive Fab clones. One clone from each format, designated as m253 and m254, respectively, was selected for further analysis. Sequence analysis revealed that m252 has heavy and light chains originated from germlines IGHV1-2*02 and IGKV1-16*01 respectively. M253 originated from IGHV1-18*01 and IGKV1-9*01, while m254 was from IGHV3-43*01 and IGKV1-27*01. The mutational rate ranged from zero to less than 10%. This is typical for antibodies isolated from naive human libraries by panning against viruses causing acute infection in contrast to neutralizing antibodies selected from immune human libraries by panning against HIV-1 which causes chronic infection (Xiao, X. et al., 2009, Biochem. Biophys. Res. Commun. 390, 404-409). Each of the clones was then transformed into HB2152 cells and the respective Fab was expressed and purified (FIG. 1a). After conversion to IgG1 expressing clones, the three antibody clones were transiently transfected into Freestyle HEK 293F cells, and the expressed IgG1s were purified (FIG. 1c).

Example 2

Binding of the Selected mAbs as Fabs and IgG1s to Their Antigens

To determine both the specificity and affinity of the selected antibodies, ELISA with both Fab and IgG formats were conducted as described in the methods. All Fabs and IgGs bound to their respective antigens specifically without cross-reaction to other antigens tested (FIGS. 1b and d). Anti-F1 Fab and IgG have apparent affinities in the low and sub-nM range, respectively. Both m253 and m254 Fabs have apparent affinities of approximately 100 nM (FIGS. 1b and d). Their IgGs however have sub-nM apparent affinities (avidities). The avidity effect is very pronounced for all three antibodies.

Example 3

Figure 2:
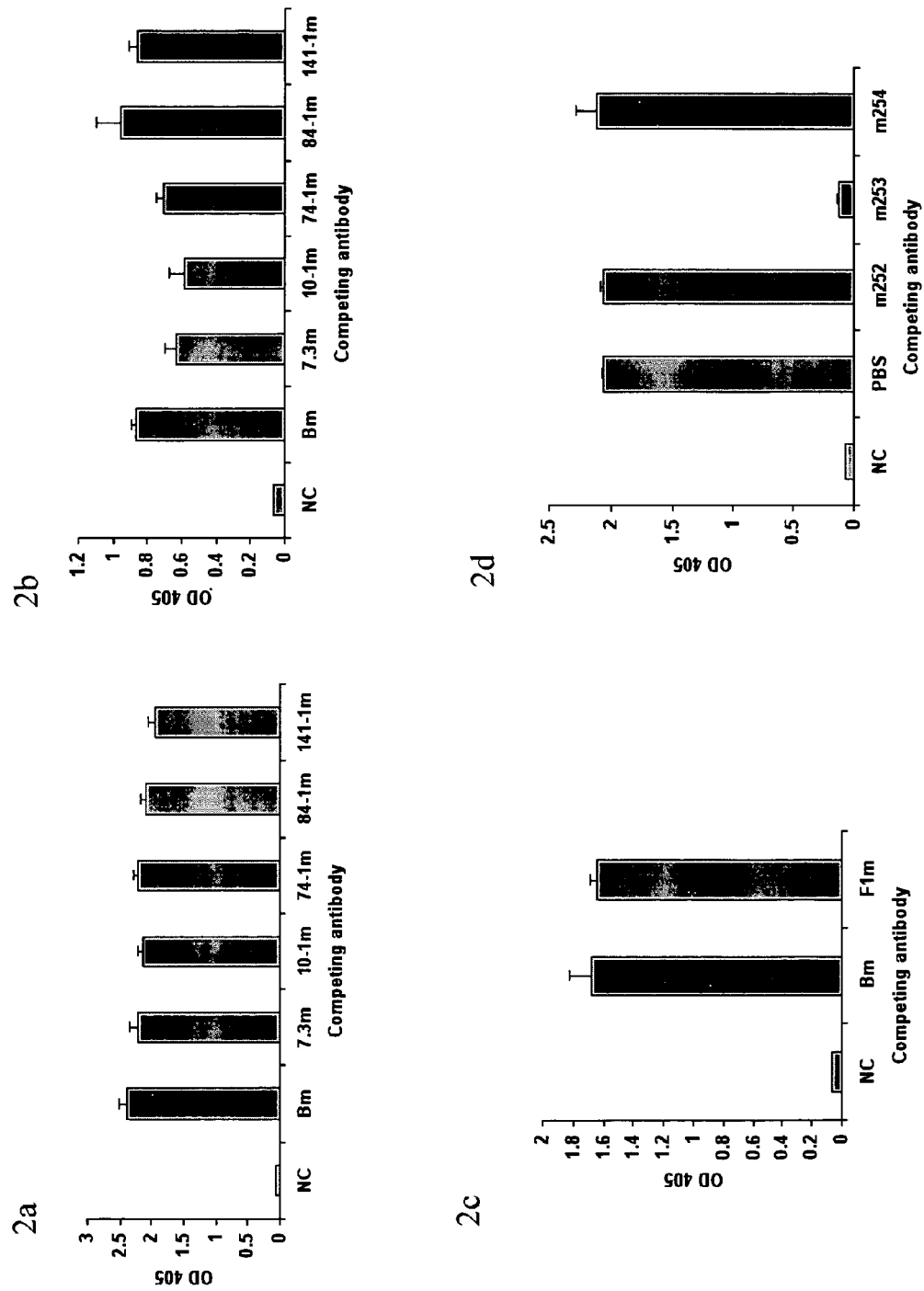
FIGS. 2a, 2b, 2c, and 2d. Epitope binding analysis of human Fab fragments by competition-ELISA. a and b, Fab fragments anti-V m253 and m254 binding to the V-antigen was analyzed by competition with equal amounts of control IgG, mouse anti-Bm (mouse anti-*Burkholderia mallei* antibody), and five other mouse anti-V mAbs as described in materials and methods, respectively. The amount of bound human Fab fragment was then determined. c. Lack of competition between human Fab anti-F1 fragment and mouse anti-F1 mAb (mouse mAb F1-04-A-G1). d. Competition among human antibodies. Fab fragments m252, m253, and m254 were mixed with equal amounts of IgG m253 and applied to an ELISA plate coated with their respective antigens. The amount of bound Fab fragments was determined.

Low Level of Competition Between the Human Anti-F1 and Anti-V Fabs and Mouse Anti-F1 and Anti-V Mabs The three human anti-plague Fabs were used in competition-ELISAs against a panel of mouse anti-plague mAbs. The mouse anti-plague mAbs included the anti-F1 mAb F1-04-A-G1, and five anti-V mAbs, which included the anti-V mAb 7.3 that was highly protective (see FIGS. 4-7 below). We found no apparent competition between the human anti-V m253 Fab and the mouse anti-V mAbs (FIG. 2a). However, we observed some weak competition between the human anti-V m254 Fab antibody and some of the mouse anti-V mAbs (7.3m, 10-1m, and 74-1m) that we did not see with the human anti-V m253 Fab antibody (FIG. 2b). The competition between the human anti-F1 m252 Fab antibody and the mouse anti-F1 mAb was also minimal (FIG. 2c). There was also a lack of competition between the human anti-V m253 and m254 Fab antibodies, suggesting that these two human anti-V Fabs recognize different epitopes on the V-antigen (FIG. 2d). Of note, however, is that when the competition-ELISA was performed in a different fashion, namely when the human anti-F1 or anti-V mAbs were allowed to bind to the respective antigens before adding the mouse anti-F1 or anti-V mAbs, moderate competition was detected between the human anti-F1 m252 and the mouse anti-F1 mAbs, as well as between the human anti-V m253 and mouse anti-V 84-1 mAbs (data not shown).

Example 4

Epitope Mapping by Peptide-ELISA

To more closely characterize the binding of the human anti-F1 and anti-V aMbs to the F1- and V-antigens, respectively, we examined the binding of the human mAbs to two separate panels of overlapping peptides. One panel covered the full-length of the F1 antigen (27 peptides) and the other the V antigen (53 peptides). For the human anti-F1 m252 mAb, there was a weak-moderate binding signal with peptides 1 and 2, which are located at the N-terminus of the F1-antigen (FIG. 3a). This suggests that the m252 mAb may also recognize a conformational region that involves peptides 1 and 2. The binding by human anti-V m253 mAb resulted in a strong signal with peptide 2 and a weak signal with peptide 1 (FIG. 3b). Binding by anti-V m254 mAb, on the other hand, did not give a specific signal with any of the peptides, suggesting that the m254 mAb recognizes a conformational region on the V-antigen (FIG. 3c). This might explain its weak competition with mouse antibodies that recognize diverse epitopes on the V-antigen (FIG. 2b). The positive signals seen with the m253 and m254 mAbs with V-antigen peptides (numbers 19, 20, 27, and 28) are nonspecific signals generated by secondary antibody alone (Amemiya et al. unpublished). The epitopes of the mouse antibodies have also been determined by the peptide binding assay (data not shown). The data is consistent with the competition-ELISA presented in this study.

Example 5

Specific Binding of Human Anti-F1 IgG1 to *Y. Pestis*

To test if the human anti-F1 and anti-V IgGs bind their respective targets on bacterial cells, we performed flow cytometry analysis. Specific binding of the human anti-F1 IgG1 to the *Y. pestis* cell surface was detected by a flow cytometry assay. A mouse anti-B mallei IgG was used as an isotype mAb control, and the mouse anti-F1 (F1-04-A-G1) and anti-V (7.3) mAbs were used as positive IgG controls. *Y. pestis* grown at 26° C. was used as an anti-F1 mAb negative control. *E. coli* grown at 37° C. was used as a specificity control for anti-F1 and anti-V IgGs. Our results indicate that both the mouse anti-F1 Flm mAb and human anti-F1 m252 mAb bound specifically to *Y. pestis* grown at 37° C. and not to the same strain grown at 26° C. (Table 1). Neither did they bind to a control *E. coli* strain grown at 37° C. (Table 1). This is consistent with previous reports that the expression of the F1-antigen is regulated by temperature (37° C.), and it is not expressed at RT. The human anti-V m254 mAb showed minor binding to the *Y. pestis* grown at 37° C., although we do not normally see this with the human or mouse anti-V mAbs (Amemiya, unpublished). The anti-F1 Flm mAb (F1-04-A-G1) showed similar binding to the *Y. pestis* whole-cell.

TABLE 1

Binding of Human and Mouse mAbs to *Y. pestis* whole cells determined by flow cytometry

| | Percent of Binding by Human and Mouse mAbs | | | | |
|---|---|---|---|---|---|
| Culture Conditions (Temp.) | Unstained Cells | m254 Human αV mAb | F1-04-A-G1 (F1m) Mouse α F1 mAb | m252 Human αF1 mAb | Mouse IgG1 Isotype Control |
| *Y. pestis* (26° C.) | 0.12% | 0.32% | 10.56% | 0.57% | 0.38% |
| *Y. pestis* (37° C.) | 0.39% | 5.39% | 76.40% | 30.25% | 0.62% |
| *E. coli* (37° C.) | 0.51% | 0.23% | 1.34% | 0.43% | 0.46% |

To further confirm the binding data we used immunofluorescence detection of human anti-F1 IgG1 binding to the *Y. pestis* cell surface. The mouse anti-*B mallei* IgG was used as a nonspecific isotype control.

The mouse anti-V mAb 7.3 was used as a negative IgG control. The mouse anti-F1 mAb (F1-04-A-G1) was used as a positive control. The results were consistent with the flow cytometry data, where only the mouse and human anti-F1 mAb bound to *Y. pestis* whole-cells (Table 2). Neither the human anti-V m254 mAb or control samples showed significant binding to *Y. pestis* (Table 2). The slight binding shown with the human anti-V m254 to *Y. pestis* was considered not significant when compared to the lack of binding shown by mAb 7.3 or binding by the mouse or human anti-F1 mAbs.

TABLE 2

Binding of anti-F1 and anti-V mAb to *Y. pestis* determined by fluorescent microscopy.

| Monoclonal Antibodies | Microscopic Conditions | |
|---|---|---|
| | Phase Contrast | FITC Fluorescence |
| Nonspecific mAb | – | – |
| F1m | – | ++++ |
| m252 | – | ++++ |
| m254 | +/–* | +/– |
| No primary Ab, secondary only | – | – |

*Seen in both conditions

Example 6

Human Anti-F1 and V mAbs Protect Synergistically Against a *Y. Pestis* Challenge in a Bubonic Plague Model The ability of the human anti-F1 and anti-V mAbs to passively protect mice against a *Y. pestis* infection was evaluated in a bubonic plague model. The human anti-F1 and V mAbs were used either separately or together in different combinations. When human mAbs m252 and m253 and m254 were given to mice separately before challenge with *Y. pestis* CO92, only the human anti-F1(m252) mAb showed some efficacy. The mean-time-to-death (MTD) in the m252 mAb-treated mice was shifted to 13.0 days (1/6 survivors) when compared with mice given normal mouse serum (NMS), which had a MTD of 7.0 days (0/6 survivors) (FIG. 4). Unlike m252, however, the human anti-V mAbs m253 and m254 did not show any significant protection [mean-time-to-death (MTD) of 6.7 days (0/6 survivors) and 7.3 days (0/6 survivors), respectively] when compared to the NMS-treated mice. The mouse anti-F1 (F1m) and anti-V (7.3m) control mAbs both passively protected all (6/6) mice under the same challenge conditions (MTD of 21 days). When both human anti-V mAbs were given to mice passively (FIG. 5), no improvement in protection after challenge was observed (MTD of 6.8 days, 0/6 survivors), which was similar to that seen with the NMS-treated mice (MTD of 7.3 days, 0/6 survivors). However, when the human anti-F1 m252 mAb (MTD of 11.3 days, 2/6 survivors) was given together with the two human anti-V m253 and m254 mAbs, a greater number of mice were passively protected (MTD 14.0, 5/6 survivors) than when the antibodies were used separately, suggesting a synergistic effect.

Example 7

Delaying Time of Delivery of Human Anti-Plague mAbs Provided Better Protection Against a Plague Challenge One possible reason we observed less protection with the human anti-F1 and anti-V mAbs in the mouse plague model was that the level of the human IgGs may not have been sustained in the mouse over time compared to the mouse IgG mAbs. We tested this hypothesis in two separate studies. We first examined the concentration of the human antibody in mice directly, by measuring the level of m252 (anti-F1) and m253 (anti-V) in serum after they were given the human mAbs by i.p. injection. Mouse sera were collected at different time points after the initial dosing and human IgG levels were monitored by direct ELISA. As seen in FIG. 6A, the anti-F1 m252 mAb appeared to have a half-life of approximately 8 days, and the half-life of m253 mAb was approximately 10 days. After 21 days, the levels of these two human antibodies were undetectable. In contrast, the level of both the mouse anti-F1 (Flm) and anti-V (7.3m) mAbs may have decreased initially like the human anti-plague mAbs, but after 21 days, the levels were still approximately 40-50% of the initial concentration (FIG. 6B). The half-life of human IgG mAbs in mice reported here is similar to what was found in another study where human mAbs were used against another bio-threat agent (Albrecht, M. T. et al., 2007, Infect. Immun. 75, 5425-5433). In contrast, a human IgG molecule would have an average serum half-life of 21 days in a human (Turner, A., 2001, Antibodies. In Roitt, I. M. et al., Eds., *Immunology*, New York, N.Y., Mosby, pp 65-86).

Because of these findings we then administered the anti-F1 m252 mAb at different time points relative to the time of challenge. While the original regimen provided consistently modest protection, administration of the human m252 mAb 24 and 48 hours post-challenge provided increasing protection with the 48 hours schedule provided complete protection (FIG. 7). Antibody administration at even later time points was not performed since mice began to die 3-4 days after challenge without any treatment. However, we did evaluate the effect of a second dose of antibody at a later time point. In this group, mice first received an initial dose of human anti-F1 m252 mAb 24 hour before challenge as was done with the earlier protocols. These mice then received a second dose of the human anti-F1 m252 mAb 5 days after challenge. There was an increase in both the number of survivors (5/6) and MTD (20 days) approaching the efficacy displayed by a single dose administered 48 hour after challenge. These data suggest that the optimum serum concentration of the human IgG1s was critically dependent on the time of administration, and that the optimum concentration of the human anti-plague IgG1s in turn determined the outcome of the treatment protocol.

Discussion

Antibiotics have been at the forefront of combating bacterial infection for decades with great success. However, the development of new antibiotics is struggling to keep pace with the emergence of drug resistance bacterial strains, for example as in *Y. pestis* (Galimand, M. et al., 1997, supra). There has been an intense interest in developing antibody-based therapies as alternative method of treatment (Casadevall, A., 2002, supra). Initially, it was mostly limited to treating cancer or immune disorders. The use of antibody-based therapy as an anti-infectious agent is being increasingly recognized and explored, thanks to a better understanding of the immune system and advancement of technologies (Xiao and Dimitrov, 2007, Recent Patents Anti-Infect. Drug Disc. 2, 171-177). In this report we described the first isolation of fully human mAbs against the *Y. pestis* virulence factors F1- and V-antigens. Previous studies have shown that mouse mAbs can be effective in protecting mice against *Y. pestis* (Anderson, G. W. et al., 1997, supra; Hill, J. et al., 1997, supra; Hill J. et al., 2003, supra). However, because they are mouse mAbs they are not safe to use in their present form in humans (Hwang and Foote, 2005, Methods 36, 3-10). Of particular concern is the immune reaction against mouse primary antibody sequences in human system. This may lead to severe adverse effect and at the same time reduce the potential benefits. It is highly desirable to have fully human antibodies for these reasons. The fully human anti-F1 (m252) reported here displayed moderate to good protection against a bubonic plague challenge with *Y. pestis* CO92. On the other hand, the two anti-V mAbs (m253, m254) when used separately did not show any efficacy, but when they were used together with m252, the combination of the human anti-plague mAbs resulted in better protection overall, suggesting a synergistic effect between the antibodies. A similar effect was reported in studies using mouse anti-F1 and anti-V mAbs in a mouse model of plague (Hill, J. et al., 2003, supra). Further in our case with the human anti-F1 mAbs, when we altered the time of delivery of the human anti-plague mAb, we saw that a greater protection against a plague challenge could be achieved. This implied that the maintenance of serum concentration of the human mAbs in the mouse was possibly one critical factor for better protection. Kinetic studies revealed that indeed the serum concentration of the human antibodies dropped further than the mouse anti-plague mAbs over the course of the study. It is also plausible that the human anti-plague mAbs might bind to other mouse antigens nonspecifically, thus decreasing the amount of free circulating human anti-plague antibody in the mouse.

Another important underlying factor for efficient protection by antibodies is the epitopes the antibodies recognize. Although the human anti-F1 (m252) mAb appeared to bind to the same region as the mouse antiF1, which was at the amino-terminal end of the F1-antigen (data not shown), we could not demonstrate direct competition between these two antibody species. This observation may be the result of the nature of the antibody binding site or epitope, because several mouse mAbs isolated independently recognized the same region or epitope on the F1-antigen, behaved in the same manner (data not shown). It may be that once these mAbs bound to the amino-terminal end of the F1-antigen, they may not readily come off the protein or may dissociate very slowly. Whether this is because the binding site involved both linear and conformational sites is not known, but both the mouse and human anti-F1 mAbs bound to the whole anti-F1 antigen very well, but only weakly—moderately to the 5'-peptides. Nevertheless, the human m252 mAb was as protective as the mouse anti-F1 mAb once the administration schedule for delivery of the human mAb was altered. It has also been reported that a neutralizing epitope on the V-antigen was located in a region spanning amino acids 135 to 275, and a possible minor, secondary neutralizing epitope exists near the amino-terminal region of the V-antigen (Hill, J. et al., 1997, supra). Neither of our human anti-V antibodies reported here competed with the mouse anti-V antibodies efficiently. The minor competition between the human anti-V Fab antibody and the mouse anti-V antibodies suggests that the recognition site of the human anti-V antibodies is slightly different or they may partially share conformational binding site. These differences might be one reason for their inability to protect as efficiently as the human anti-F1 m252 mAb.

Exactly how the human anti-F1 252m mAb is able to protect mice may be directly related to the presence of F1 antigen on the surface of the plague organism. The F1-antigen has been been reported to be anti-phagocytic (Cavanaugh and Randall, 1959, J. Immunol. 83, 348-363; Du, Y. et al., 2002, Infect. Immun. 70, 1453-1460). The ability of macrophages to take up the plague organism is directly related to the lack of the F1-antigen, and resistance to phagocytosis is related to the presence of the F1-antigen. The binding of the human anti-F1 252m mAb to the surface of the plague bacilli or opsonization may trigger phagocytosis of encapsulated bacilli into macrophages, thereby allowing phagocytic cells to clear the host of the pathogen.

The exact mechanism by how the V-antigen exerts it virulence is not completely known. There are reports showing that V-antigen is secreted into the growth medium and the secretion is important for virulence (Lawton, W. D. et al., 1963, J. Immunol. 91, 179-184; Broms, J. E. et al., 2007, J. Bacteriol. 189, 8417-8429). The secretion of V-antigen in the medium has been described to be dependent on contact with the host cell, and also directed into the host cell by a *Yersinia* outer proteins (Yops) dependent secretion (Ysc) type III system (TTSS) (Mueller, C. A. et al., 2005, Science 310, 674-676; Pettersson, J. et al., 1999, Mol. Microbiol. 32, 961-976; Fields, K. A. et al., 1999, Infect. Immun. 67, 4801-4813). It also has been suggested that V-antigen may enter the cell by endocytosis besides utilizing the Ysc TTSS (DiMezzo, T. L. et al., 2009, PLoS ONE 4: e6281). Once inside the host-cell, the exact target of V-antigen is not clear or what host proteins interact with the intracellular V-antigen (DiMezzo, T. L. et al., 2009, supra). What is the most important method of entry into the cell by V-antigen or if the method influences the possible mechanism of pathogenisis of V-antigen still remains to be solved. Nevertheless, there is some evidence that anti-V antibodies enhance phagocytosis through possibly the Fc receptor, and thereby block Yop delivery into the host cell, and preventing Ysc dependent TTSS injection of V-antigen into the host cell (Weeks, S. et al., 2002, Microbiol. Path. 32, 227-237; Cowan, C. et al., 2005, Infect. Immun. 73, 6127-6137).

In this study, however, we were not able to detect binding of the human anti-V mAbs on the surface of Y. pestis cells by flow cytometry or fluorescent microscopy, suggesting that the V-antigen was not on the bacterial cell surface under the conditions used in our studies or the expression level of V-antigen was below the level of detection. As has been discussed previously, however, the presence of V-antigen on the surface of the cell may be dependent on contact with the eukaryotic host cell. The highly specific region of the neutralizing epitope(s) on the V-antigen suggests a possible ligand-receptor interaction between the V-antigen and a cellular factor. This indicates that perhaps the V-antigen exerts its biological effect through mechanisms other than mediating the TTSS pathway.

In conclusion, the human anti-plague antibodies reported here represent perhaps the ones that are closest to practical clinical usage. Not only will they be safer due to their fully human nature, but also possibly more efficient due to a likely longer half-life in a human system. Also, intravenous application of the antibodies in humans may rapidly deliver anti-plague neutralizing therapeutic treatment that can augment antibiotic treatment in plague-exposed individuals. Finally, the affinity of all three antibodies can be further increased using readily available techniques, thus reducing the dose required for efficient protection. The successful development of these three human anti-plague antibodies suggests that new and more potent anti-V antibodies can be potentially developed using the same approach but with restricted V-antigen subunit fragments containing the critical neutralizing epitopes, and perhaps other virulent factors.

What is claimed is:

1. A composition comprising a combination of F1 and V antibodies, wherein said F1 antibodies comprise an F1 antibody having the amino acid sequence of SEQ ID NO: 3, SEQ ID NO:5, or an antibody fragment that retains the complimentarity determining regions (CDRs) of SEQ ID NO: 3, SEQ ID NO:5.

2. The composition of claim 1 wherein said V antibodies comprise an antibody having the amino acid sequence of SEQ ID NO: 9, SEQ ID NO:11, or antibody fragment thereof that retains the complimentarity determining regions (CDRs) of SEQ ID NO: 9, SEQ ID NO:11.

3. The composition of claim 1 wherein said V antibodies comprise an antibody having amino acid sequence of SEQ ID NO: 13, SEQ ID NO:15, or an antibody fragment thereof that retains the complimentarity determining regions (CDRs) of SEQ ID NO: 13, SEQ ID NO:15.

4. The composition of claim 3 wherein said V antibodies comprise a second V antibody having the amino acid sequence of SEQ ID NO: 9, SEQ ID NO:11, or antibody fragment thereof that retains the complimentarity determining regions (CDRs) of SEQ ID NO: 9, SEQ ID NO:11.

5. The composition of claim 1 wherein said composition is a pharmaceutical composition.

6. The composition of claim 2 wherein said composition is a pharmaceutical composition.

7. The composition of claim 3 wherein said composition is a pharmaceutical composition.

8. The composition of claim 4 wherein said composition is a pharmaceutical composition.

9. A method for detecting, in a sample, Y. pestis, said method comprising:
(i) incubating the sample with an effective amount of the composition of claim 1, under conditions which allow the formation of an antibody-Y. pestis complex; and
(ii) detecting the antibody-Y. pestis complex wherein the presence or absence of the complex indicates the presence or absence or said Y. pestis in the sample.

10. A method for detecting Y. pestis according to claim 9 wherein said sample is a biological sample.

11. A method for treating Y. pestis infection comprising administering to a patient in need of said treatment an amount of the composition of claim 5 sufficient to effect said treatment.

12. A method for treating Y. pestis infection comprising administering to a patient in need of said treatment an amount of the composition of claim 6 sufficient to effect said treatment.

13. A method for treating Y. pestis infection comprising administering to a patient in need of said treatment an amount of the composition of claim 7 sufficient to effect said treatment.

14. A method for treating Y. pestis infection comprising administering to a patient in need of said treatment an amount of the composition of claim 8 sufficient to effect said treatment.

15. A method for detecting, in a sample, F1 from Y. pestis, said method comprising:
(i) incubating the sample with an effective amount of the composition of claim 1, under conditions which allow the formation of an antibody-F1 complex; and
(ii) detecting the antibody-F1 complex wherein the presence or absence of the complex indicates the presence or absence or said F1 from Y. pestis in the sample.

16. A method for detecting, in a sample, V antigen from Y. pestis, said method comprising:
(i) incubating the sample with an effective amount of a composition comprising V antibodies having the amino acid sequence of SEQ ID NO: 9, SEQ ID NO:11, or antibody fragment thereof that retains the complimentarity determining regions (CDRs) of SEQ ID NO: 9, SEQ ID NO:11, and/or V antibodies having amino acid sequence of SEQ ID NO: 13, SEQ ID NO:15, or an antibody fragment thereof that retains the complimentarity determining regions (CDRs) of SEQ ID NO: 13, SEQ ID NO:15, under conditions which allow the formation of an antibody-V antigen complex; and
(ii) detecting the antibody-V antigen complex wherein the presence or absence of the complex indicates the presence or absence or said V antigen from Y. pestis in the sample.

* * * * *